US012426772B2

(12) United States Patent
Scheib et al.

(10) Patent No.: US 12,426,772 B2
(45) Date of Patent: Sep. 30, 2025

(54) ARTICULATING INTRODUCER CANNULA FOR SURGICAL SCOPE IN ROBOTIC SYSTEM

(71) Applicant: Auris Health, Inc., Redwood City, CA (US)

(72) Inventors: Charles J. Scheib, Loveland, OH (US); Clinton Denlinger, Cincinnati, OH (US); Jeffrey S. Swayze, West Chester, OH (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/941,063

(22) Filed: Sep. 9, 2022

(65) Prior Publication Data

US 2024/0081627 A1    Mar. 14, 2024

(51) Int. Cl.
*A61B 1/01*    (2006.01)
*A61B 1/00*    (2006.01)
*A61B 1/313*   (2006.01)

(52) U.S. Cl.
CPC ............ *A61B 1/01* (2013.01); *A61B 1/00149* (2013.01); *A61B 1/00154* (2013.01); *A61B 1/3132* (2013.01)

(58) Field of Classification Search
CPC ... A61B 1/00149; A61B 1/00154; A61B 1/01; A61B 1/3132; A61B 17/3417; A61B 1/00135; A61B 1/00142; A61B 1/0016; A61B 1/0055; A61B 1/0125; A61B 1/018
See application file for complete search history.

(56) References Cited

U.S. PATENT DOCUMENTS

| | | | |
|---|---|---|---|
| 5,419,311 A | * | 5/1995 | Yabe ...................... A61B 1/015 600/124 |
| 9,737,371 B2 | | 8/2017 | Romo et al. |
| 10,667,871 B2 | | 6/2020 | Romo et al. |
| 10,792,069 B2 | | 10/2020 | Hall et al. |
| 10,820,924 B2 | | 11/2020 | Hall et al. |
| 10,856,724 B2 | | 12/2020 | Miller |

(Continued)

OTHER PUBLICATIONS

U.S. Appl. No. 17/941,057, filed Sep. 9, 2022 by Scheib et al., entitled: "Remotely Driven Camera in Robotic System."

(Continued)

*Primary Examiner* — Aaron B Fairchild
(74) *Attorney, Agent, or Firm* — Frost Brown Todd LLP

(57) ABSTRACT

An apparatus includes a proximal structure configured to be positioned extracorporeally relative to a patient, and a distal structure extending distally from the proximal structure and configured to be passed through a body wall and into a body cavity of the patient. The distal structure cooperates with the primary structure to define a primary axis and a working channel sized and configured to receive and guide a surgical scope shaft distally therethrough along the primary axis. The proximal structure has a greater maximum dimension in a direction transverse to the primary axis than the distal structure. The apparatus further includes an articulation feature at a distal end of the distal structure that is configured to articulate relative to the proximal structure to direct the surgical scope shaft along a secondary axis that is angled relative to the primary axis.

11 Claims, 33 Drawing Sheets

(56) References Cited

U.S. PATENT DOCUMENTS

| | | | |
|---|---|---|---|
| 10,939,937 | B2 | 3/2021 | Terefe et al. |
| 10,945,904 | B2 | 3/2021 | Ruiz |
| 11,179,213 | B2 | 11/2021 | Huang et al. |
| 11,197,728 | B2 | 12/2021 | DeFonzo et al. |
| 11,432,709 | B2 | 9/2022 | Yoshinaga et al. |
| 11,633,211 | B2 | 4/2023 | Muthuchidambaram et al. |
| 11,744,654 | B2 | 9/2023 | Rohr Daniel et al. |
| 2008/0287963 | A1* | 11/2008 | Rogers .................. A61B 1/009 600/111 |
| 2012/0016191 | A1 | 1/2012 | Ito et al. |
| 2013/0197535 | A1 | 8/2013 | Okada |
| 2016/0199140 | A1* | 7/2016 | Gombert ............ A61B 1/00009 606/130 |
| 2019/0350660 | A1 | 11/2019 | Moll et al. |
| 2020/0276416 | A1* | 9/2020 | Wheeler ............ A61B 17/3415 |
| 2021/0401527 | A1 | 12/2021 | Hassan |
| 2022/0304549 | A1 | 9/2022 | Iijima |
| 2023/0371793 | A1 | 11/2023 | Magno et al. |

OTHER PUBLICATIONS

U.S. Appl. No. 17/941,059, filed Sep. 9, 2022 by Leclere et al., entitled: "Flexible Articulating Introducer Cannula for Surgical Scope in Robotic System."
U.S. Appl. No. 17/941,062, filed Sep. 9, 2022 by Scheib et al., entitled: "Bent Introducer Cannula for Surgical Scope in Robotic System."
U.S. Appl. No. 17/941,057.
U.S. Appl. No. 17/941,059.
U.S. Appl. No. 17/941,062.

* cited by examiner

ARTICULATING INTRODUCER CANNULA FOR SURGICAL SCOPE IN ROBOTIC SYSTEM

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically assisted surgery. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, cauterizing tissue, and/or other functions.

While several robotic surgical systems and associated components have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
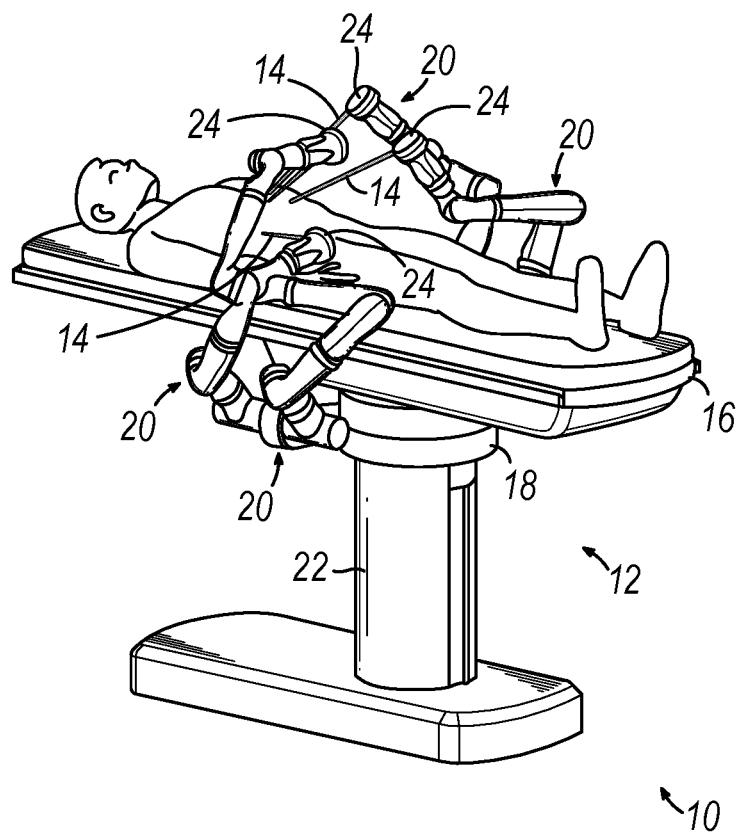
FIG. 1 depicts a perspective view of a first example of a robotic system configured for a laparoscopic procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "side," "upwardly," and "downwardly" also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

In addition to performing the breadth of procedures, the robotically-enabled medical system may provide additional benefits, such as enhanced imaging and guidance to assist the medical professional. Additionally, the robotically-enabled medical system may provide the medical professional with the ability to perform the procedure from an ergonomic position without the need for awkward arm motions and positions. Still further, the robotically-enabled medical system may provide the medical professional with the ability to perform the procedure with improved ease of use such that one or more of the instruments of the robotically-enabled medical system may be controlled by a single operator.

I. Example of Robotically-Enabled Medical System

FIG. 1 shows an example of a robotically-enabled medical system, including a first example of a robotic system (10). Robotic system (10) of the present example includes a table system (12) operatively connected to a surgical instrument (14) for a diagnostic and/or therapeutic procedure in the course of treating a patient. Such procedures may include, but are not limited, to bronchoscopy, ureteroscopy, a vascular procedure, and a laparoscopic procedure. To this end, surgical instrument (14) is configured for a laparoscopic procedure, although it will be appreciated that any instrument for treating a patient may be similarly used. At least part of robotic system (10) may be constructed and operable in accordance with at least some of the teachings of any of the various patents, patent application publications, and patent applications that are cited herein.

A. Example of Robotic System with Annular Carriage

As shown in FIG. 1, robotic system (10) includes table system (12) having a platform, such as a table (16), with a plurality of carriages (18) which may also be referred to herein as "arm supports," respectively supporting the deployment of a plurality of robotic arms (20). Robotic system (10) further includes a support structure, such as a column (22), for supporting table (16) over the floor. Table (16) may also be configured to tilt to a desired angle during use, such as during laparoscopic procedures. Each robotic arm (20) includes an instrument driver (24) configured to removably connect to and manipulate surgical instrument (14) for use. In alternative examples, instrument drivers (24) may be collectively positioned in a linear arrangement to support the instrument extending therebetween along a "virtual rail" that may be repositioned in space by manipulating the one or more robotic arms (20) into one or more angles and/or positions. In practice, a C-arm (not shown) may be positioned over the patient for providing fluoroscopic imaging.

In the present example, column (22) includes carriages (18) arranged in a ring-shaped form to respectively support one or more robotic arms (20) for use. Carriages (18) may translate along column (22) and/or rotate about column (22) as driven by a mechanical motor (not shown) positioned within column (22) in order to provide robotic arms (20) with access to multiples sides of table (16), such as, for example, both sides of the patient. Rotation and translation of carriages (18) allows for alignment of instruments, such as surgical instrument (14), into different access points on the patient. In alternative examples, such as those discussed below in greater detail, robotic system (10) may include a surgical bed with adjustable arm supports including a bar (26) (see FIG. 2) extending alongside. One or more robotic arms (20) may be attached to carriages (18) (e.g., via a shoulder with an elbow joint). Robotic arms (20) are vertically adjustable so as to be stowed compactly beneath table (16), and subsequently raised during use.

Robotic system (10) may also include a tower (not shown) that divides the functionality of robotic system (10) between table (16) and the tower to reduce the form factor and bulk of table (16). To this end, the tower may provide a variety of support functionalities to table (16), such as computing and control capabilities, power, fluidics, optical processing, and/or sensor data processing. The tower may also be movable so as to be positioned away from the patient to improve medical professional access and de-clutter the operating room. The tower may also include a master controller or console that provides both a user interface for operator input, such as keyboard and/or pendant, as well as a display screen, including a touchscreen, for pre-operative and intra-operative information, including, but not limited to, real-time imaging, navigation, and tracking information. In some versions, the tower may include gas tanks to be used for insufflation.

B. Example of Robotic System with Bar Carriage

Figure 2:
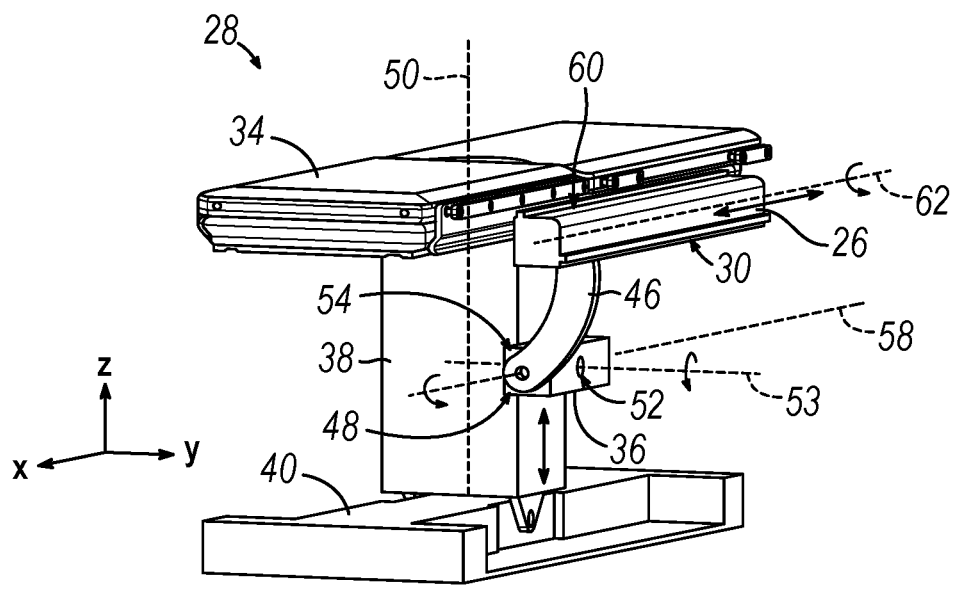
FIG. 2 depicts a perspective view of a second example of a robotic system.
Figure 3:
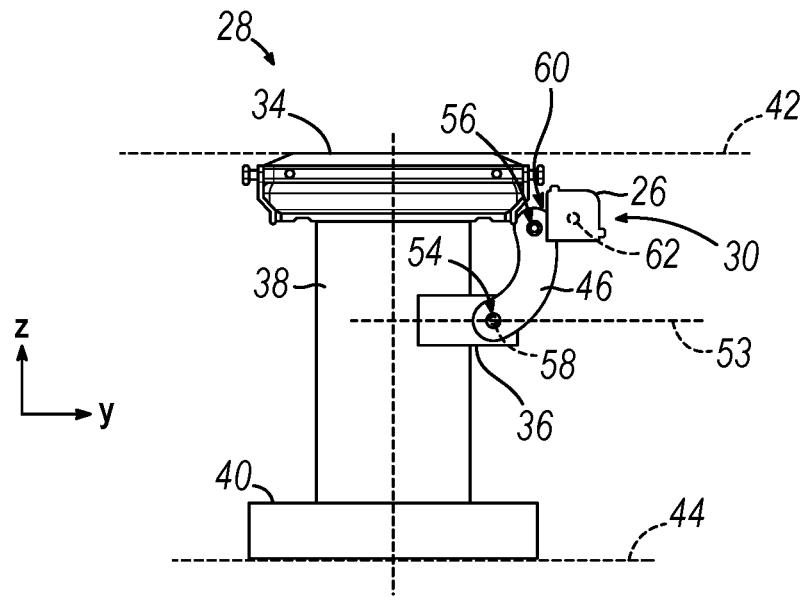
FIG. 3 depicts an end elevational view of the robotic system of FIG. 2.
Figure 4:
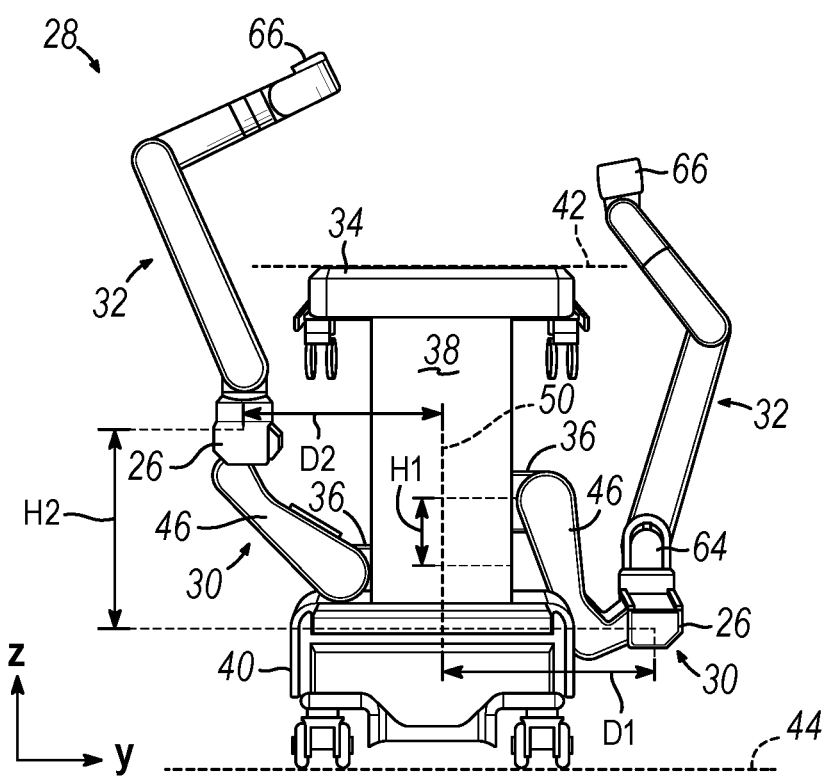
FIG. 4 depicts the end elevational view of the robotic system of FIG. 2 including an example of a pair of robotic arms.

FIGS. 2-4 show another example of a robotic system (28). Robotic system (28) of this example includes one or more adjustable arm supports (30) including bars (26) that are configured to support one or more robotic arms (32) relative to a table (34). In the present example, a single adjustable arm support (30) (FIGS. 2-3) and a pair of adjustable arm supports (30) (FIG. 4) are shown, though additional arm supports (30) may be provided about table (34). Each adjustable arm support (30) is configured to selectively move relative to table (34) so as to alter the position of adjustable arm support (30), and/or any robotic arms (32) mounted thereto, relative to table (34) as desired. Such adjustable arm supports (30) may provide high versatility to robotic system (28), including the ability to easily stow one or more adjustable arm supports (30) with robotic arms (32) beneath table (34).

Each adjustable arm support (30) provides several degrees of freedom, including lift, lateral translation, tilt, etc. In the present example shown in FIGS. 2-4, arm support (30) is configured with four degrees of freedom, which are illustrated with arrows. A first degree of freedom allows adjustable arm support (30) to move in the z-direction ("Z-lift"). For example, adjustable arm support (30) includes a vertical carriage (36). Vertical carriage (36) is configured to move up or down along or relative to a column (38) and a base (40), both of which support table (34). A second degree of freedom allows adjustable arm support (30) to tilt about an axis extending in the y-direction. For example, adjustable arm support (30) includes a rotary joint, which allows adjustable arm support (30) to align with table (34) when table (34) is in a Trendelenburg position or other inclined position. A third degree of freedom allows adjustable arm support (30) to "pivot up" about an axis extending in the x-direction, which may be useful to adjust a distance between a side of table (34) and adjustable arm support (30). A fourth degree of freedom allows translation of adjustable arm support (30) along a longitudinal length of table (34), which extends along the x-direction. Base (40) and column (38) together support table (34) relative to a support surface, which is shown along a support axis (42) above a floor axis (44) in the present example. While the present example shows adjustable arm support (30) mounted to column (38), arm support (30) may alternatively be mounted to table (34) or base (40).

As shown in the present example, adjustable arm support (30) includes vertical carriage (36), a bar connector (46), and bar (26). To this end, vertical carriage (36) attaches to column (38) by a first joint (48), which allows vertical carriage (36) to move relative to column (38) (e.g., such as up and down a first, vertical axis (50) extending in the z-direction). First joint (48) provides the first degree of freedom ("Z-lift") to adjustable arm support (30). Adjustable arm support (30) further includes a second joint (52), which provides the second degree of freedom (tilt) for adjustable arm support (30) to pivot about a second axis (53) extending in the y-direction. Adjustable arm support (30) also includes a third joint (54), which provides the third degree of freedom ("pivot up") for adjustable arm support (30) about a third axis (58) extending in the x-direction. Furthermore, an additional joint (56) mechanically constrains third joint (54) to maintain a desired orientation of bar (26) as bar connector (46) rotates about third axis (58). Adjustable arm support (30) includes a fourth joint (60) to provide a fourth degree of freedom (translation) for adjustable arm support (30) along a fourth axis (62) extending in the x-direction.

FIG. 4 shows a version of robotic system (28) with two adjustable arm supports (30) mounted on opposite sides of table (34). A first robotic arm (32) is attached to one such bar (26) of first adjustable arm support (30). This first robotic arm (32) includes a connecting portion (64) attached to a first bar (26). Similarly, a second robotic arm (32) includes connecting portion (64) attached to the other bar (26). As shown in FIG. 4, vertical carriages (36) are separated by a first height (H1), and bar (26) is disposed a second height (H2) from base (40). The first bar (26) is disposed a first distance (D1) from vertical axis (50), and the other bar (26) is disposed a second distance (D2) from vertical axis (50). Distal ends of first and second robotic arms (32) respectively include instrument drivers (66), which are configured to attach to one or more instruments such as those discussed below in greater detail.

In some versions, one or more of robotic arms (32) has seven or more degrees of freedom. In some other versions, one or more robotic arms (32) has eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and connecting portion (64) (1-degree of freedom including translation). In some versions, the insertion degree of freedom is provided by robotic arm (32); while in some other versions, an instrument such as surgical instrument includes an instrument-based insertion architecture.

Figure 5:
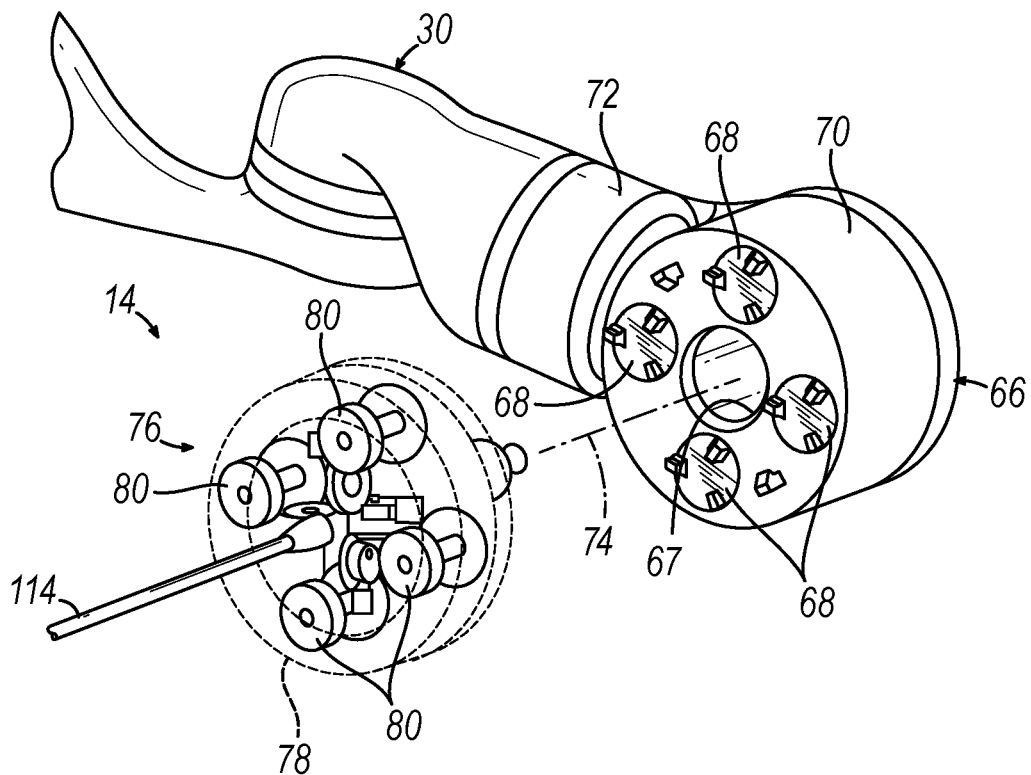
FIG. 5 depicts a partially exploded perspective view of the robotic arm of FIG. 4 having an instrument driver and an example of a surgical instrument.

FIG. 5 shows one example of instrument driver (66) in greater detail, with surgical instrument (14) removed therefrom. Given the present instrument-based insertion architecture shown with reference to surgical instrument (14), instrument driver (66) further includes a clearance bore (67) extending entirely therethrough so as to movably receive a portion of surgical instrument (14) as discussed below in greater detail. Instrument driver (66) may also be referred to herein as an "instrument drive mechanism," an "instrument device manipulator," or an "advanced device manipulator" (ADM). Instruments may be configured to be detached, removed, and interchanged from instrument driver (66) for individual sterilization or disposal by the medical professional or associated staff. In some scenarios, instrument drivers (66) may be draped for protection and thus may not need to be changed or sterilized.

Each instrument driver (66) operates independently of other instrument drivers (66) and includes a plurality of rotary drive outputs (68), such as four drive outputs (68), also independently driven relative to each other for directing operation of surgical instrument (14). Instrument driver (66) and surgical instrument (14) of the present example are aligned such that the axes of each drive output (68) are parallel to the axis of surgical instrument (14). In use, control circuitry (not shown) receives a control signal, transmits motor signals to desired motors (not shown), compares resulting motor speed as measured by respective encoders (not shown) with desired speeds, and modulates motor signals to generate desired torque at one or more drive outputs (68).

In the present example, instrument driver (66) is circular with respective drive outputs (68) housed in a rotational assembly (70). In response to torque, rotational assembly (70) rotates along a circular bearing (not shown) that connects rotational assembly (70) to a non-rotational portion (72) of instrument driver (66). Power and controls signals may be communicated from non-rotational portion (72) of instrument driver (66) to rotational assembly (70) through electrical contacts therebetween, such as a brushed slip ring connection (not shown). In one example, rotational assembly (70) may be responsive to a separate drive output (not shown) integrated into non-rotatable portion (72), and thus not in parallel to the other drive outputs (68). In any case, rotational assembly (70) allows instrument driver (66) to rotate rotational assembly (70) and drive outputs (68) in conjunction with surgical instrument (14) as a single unit around an instrument driver axis (74).

C. Example of Surgical Instrument with Instrument-based Insertion Architecture

Figure 6A:
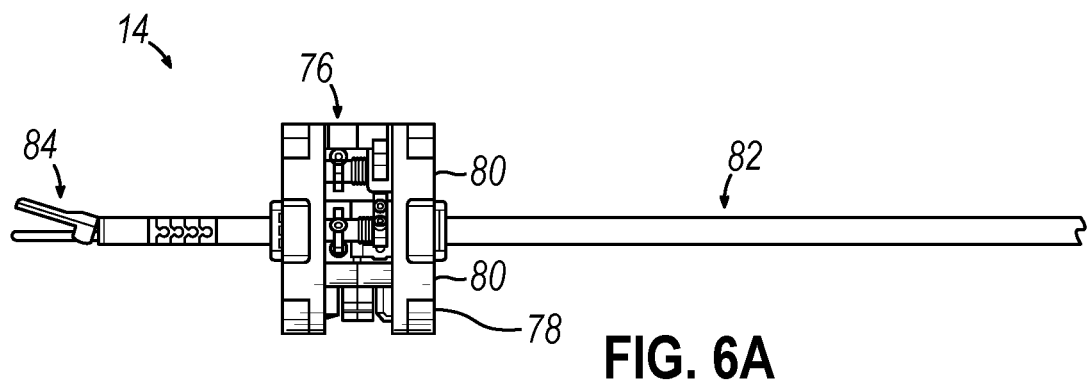
FIG. 6A depicts a side elevational view of the surgical instrument of FIG. 5 in a retracted position.
Figure 6B:
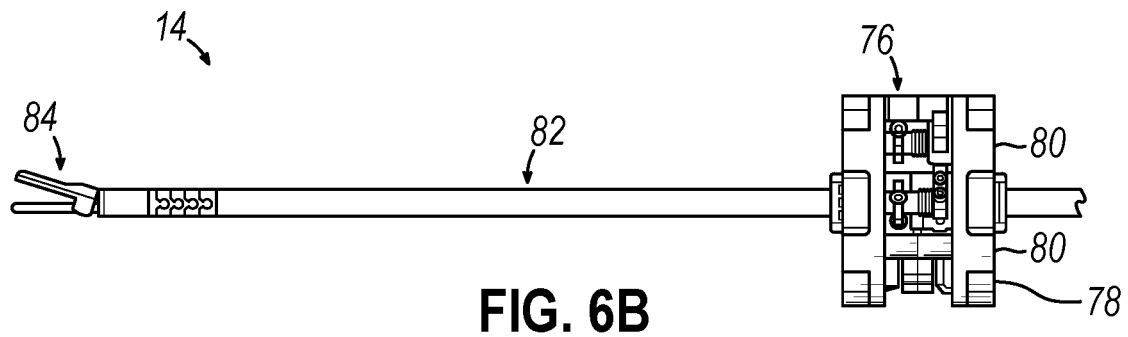
FIG. 6B depicts a side elevational view the surgical instrument of FIG. 5 in an extended position.

FIGS. 5-6B show surgical instrument (14) having the instrument-based insertion architecture as discussed above. Surgical instrument (14) includes an elongated shaft assembly (82), an end effector (84) connected to and extending distally from shaft assembly (82), and an instrument base (76) (shown with a transparent external skin for discussion purposes) coupled to shaft assembly (82). Instrument base (76) includes an attachment surface (78) and a plurality of drive inputs (80) (such as receptacles, pulleys, and spools) configured to receive and couple with respective rotary drive outputs (68) of instrument driver (66). Insertion of shaft assembly (82) is grounded at instrument base (76) such that end effector (84) is configured to selectively move longitudinally from a retracted position (FIG. 6A) to an extended position (FIG. 6B), vice versa, and any desired longitudinal position therebetween. As used herein, the retracted position is shown in FIG. 6A and places end effector (84) relatively close and proximally toward instrument base (76); whereas the extended position is shown in FIG. 6B and places end effector (84) relatively far and distally away from instrument base (76). Insertion into and withdrawal of end effector (84) relative to the patient may thus be facilitated by surgical instrument (14), although it will be appreciated that such insertion into and withdrawal may also occur via adjustable arm supports (30) in one or more examples.

When coupled to rotational assembly (70) of instrument driver (66), surgical instrument (14), comprising instrument base (76) and instrument shaft assembly (82), rotates in combination with rotational assembly (70) about the instrument driver axis (74). Since instrument shaft assembly (82) is positioned at the center of instrument base (76), instrument shaft assembly (82) is coaxial with instrument driver axis (74) when attached. Thus, rotation of the rotational assembly (70) causes instrument shaft assembly (82) to rotate about its own longitudinal axis. Moreover, as instrument base (76) rotates with instrument shaft assembly (82), any tendons connected to drive inputs (80) of instrument base (76) are not tangled during rotation. Accordingly, the parallelism of the axes of rotary drive outputs (68), rotary drive inputs (80), and instrument shaft assembly (82) allows for the shaft rotation without tangling any control tendons, and clearance bore (67) provides space for translation of shaft assembly (82) during use.

The foregoing examples of surgical instrument (14) and instrument driver (66) are merely illustrative examples. Robotic arms (32) may interface with different kinds of instruments in any other suitable fashion using any other suitable kinds of interface features. Similarly, different kinds of instruments may be used with robotic arms (32), and such alternative instruments may be configured and operable differently from surgical instrument (14).

In addition to the foregoing, robotic systems (10, 28) may be configured and operable in accordance with at least some of the teachings of U.S. Pat. No. 9,737,371, entitled "Configurable Robotic Surgical System with Virtual Rail and Flexible Endoscope," issued Aug. 22, 2017, the disclosure of which is incorporated by reference herein, in its entirety; U.S. Pat. No. 10,945,904, entitled "Tilt Mechanisms for Medical Systems and Applications," issued Mar. 16, 2021, the disclosure of which is incorporated by reference herein, in its entirety; U.S. Pub. No. 2019/0350662, entitled "Controllers for Robotically-Enabled Teleoperated Systems," published Nov. 21, 2019, issued as U.S. Pat. No. 11,179,213 on Nov. 23, 2021, the disclosure of which is incorporated by reference herein, in its entirety; U.S. Pub. No. 2020/0085516, entitled "Systems and Methods for Concomitant Medical Procedures," published Mar. 19, 2020, issued as U.S. Pat. No. 11,197,728 on Dec. 14, 2021; and/or U.S. Pub. No. 2021/0401527, entitled "Robotic Medical Systems Including User Interfaces with Graphical Representations of User Input Devices," published Dec. 30, 2021, the disclosure of which is incorporated by reference herein, in its entirety.

II. Example of a Surgical Scope Having Deflectable Shaft

In robotically assisted laparoscopic procedures, it may be desirable to mount a surgical instrument in the form of a surgical scope, also referred to as a surgical camera or a laparoscope, to a robotic arm of the robotic system to provide real-time visualization of a target surgical site and surrounding anatomical structures with the patient's body cavity during the procedure. Some conventional surgical scopes implemented in robotic systems may include an elongate rigid base and an elongate rigid shaft extending distally from the base. The surgical scope may be mounted to the head of a robotic arm, where the head is also docked directly to a cannula through which the scope shaft is inserted to access the body cavity. This configuration may tend to result in the surgical scope and its robotic arm consuming valuable space in the workspace located directly above the patient. This may ultimately tend to restrict the range of motion of the surgical scope and other robotically-controlled surgical instruments operating within this workspace, thereby limiting the reach and access of the surgical scope and the surgical instruments and risking collision between these devices and their respective robotic arms in the workspace. Accordingly, it may be desirable to provide alternative configurations of surgical scopes that promote greater reach and access of the surgical scope and accompanying surgical instruments of a robotic system.

Figure 7:
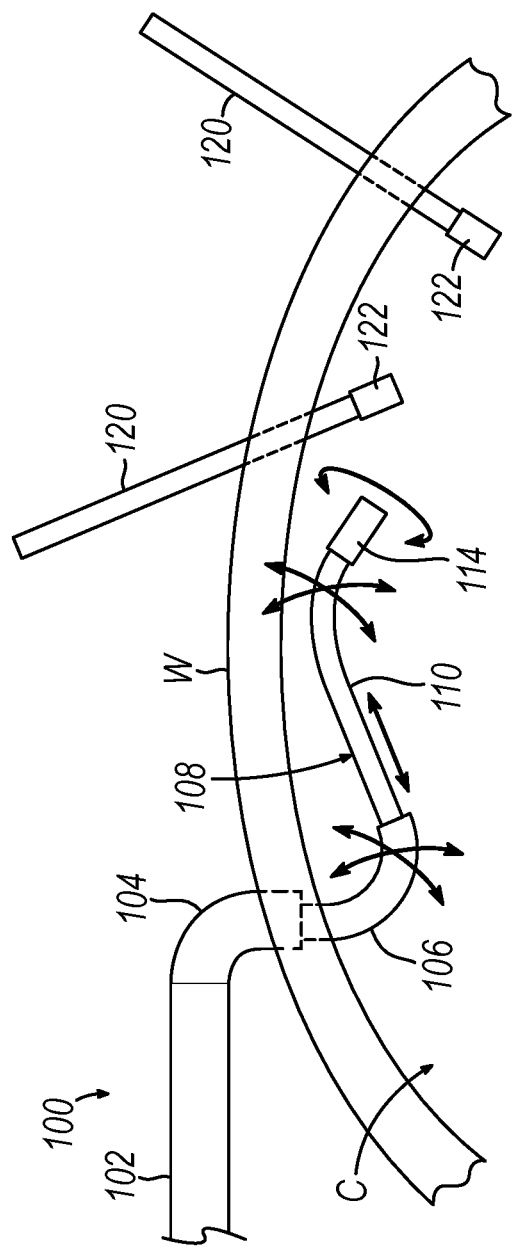
FIG. 7 depicts a schematic view of an example of a surgical scope and a pair of surgical instruments, showing a deflectable shaft portion of the surgical scope and distal ends of the surgical instruments inserted through a body wall and into a body cavity of a patient.

FIG. 7 shows an example of a surgical scope (100) that is constructed such that a portion of surgical scope (100) is non-rigid, thus enabling a base (not shown) of surgical scope (100) and its corresponding robotic arm (not shown) to be positioned remotely from the location at which the surgical scope enters through the body wall (W) and into a body cavity (C) of a patient, such as an abdominal cavity. Surgical scope (100) includes an elongate outer sheath (102) (also referred to as an "outer tube"), which may be rigid or deflectable; and a curved joint (104) at a distal end of outer sheath (102), which may also be rigid with a predefined curvature or deflectable and configured to assume a curved state as shown. As used herein, the term "deflectable" encompasses configurations that are configured to deflect relative to an initial axis, including configurations that are resiliently flexible, malleable, and/or articulatable (e.g., with a plurality of interconnected rigid links), for example. Though not shown, a proximal end of outer sheath (102) is coupled with a scope base that may be mounted to and controlled by a motorized drive mechanism (e.g., similar to instrument driver (66)) of a robotic arm.

Surgical scope (100) further includes a deflectable distal sheath (106) that extends distally from a distal end of outer sheath (102), and a scope shaft (108) that is slidably disposed within outer sheath (102) and distal sheath (106). Scope shaft (108) includes a deflectable distal shaft portion (110) (also referred to as a "leader") having an articulation section (112) and a distal tip section (114). Distal tip section (114) includes an optical module having a distally facing lens (not shown) configured to provide visualization of a target surgical site within body cavity (C). The deflectable construction of deflectable distal shaft portion (110) enables it to conform to the curvatures of curved joint (104) and distal sheath (106) as scope shaft (108) slidably advances and retracts relative to outer sheath (102) and distal sheath (106). In some versions, scope shaft (108) may further include a rigid proximal shaft portion that is directly connected to deflectable distal shaft portion (110) and that facilitates insertion and retraction of scope shaft (108). Additionally, in some other versions distal sheath (106) may be an independent structure and used with surgical scope (100).

In the present version, distal sheath (106) and scope shaft (108) cooperate to provide surgical scope (100) with six degrees of freedom, as illustrated by respective arrows in FIG. 7. Specifically, first and second degrees of freedom are provided by the ability of distal sheath (106) to articulate in first and second planes that perpendicularly intersect one another, thus providing pitch and yaw at distal sheath (106). By way of example only, one or more pull-wires, drive bands, and/or other actuation members may be used to drive articulation of distal sheath (106). A third degree of freedom is provided by the ability of scope shaft (108) to longitudinally advance and retract relative to distal sheath (106) and outer sheath (102). Fourth and fifth degrees of freedom are provided by the ability of the deflectable distal shaft portion (110) to articulate at articulation section (112) in first and second planes that perpendicularly intersect one another, thus providing pitch and yaw at articulation section (112). By way of example only, one or more pull-wires, drive bands, and/or other actuation members may be used to drive articulation of distal shaft portion (110). A sixth degree of freedom is provided by the ability of distal tip section (114) to rotate about its longitudinal axis relative to a proximal remainder of deflectable distal shaft portion (110), thus providing roll at distal tip section (114). In some other versions, the components of surgical scope (100) may be modified to include more or fewer (e.g., zero) articulation sections, each of which may be configured to articulate in one or more planes, to provide any desired quantity and arrangement of degrees of freedom. By way of example only, in other versions scope shaft (108) may include zero or two or more articulation sections (112), each configured to articulate in one or more intersecting planes.

In use, a surgeon may first create an incision in body wall (W), for example at the umbilicus, to provide access to a target surgical site located within body cavity (C). One or more other surgical instruments (120) may be inserted through body wall (W) at separate locations, for example each with a surgical cannula or other surgical access device. Each surgical instrument (120) may be mounted to a respective robotic arm and includes an end effector (122) (shown schematically) that is operable to grasp tissue, cut tissue, staple tissue, seal tissue, and/or provide other functionality at the target surgical site. Distal sheath (106) of surgical scope (100) is inserted distally through the incision in body wall (W) into body cavity (C) while outer sheath (102) remains supported by a respective robotic arm. Surgical scope (100) may then be actuated, for example by a drive mechanism of the respective robotic arm, to advance scope shaft (108) distally through outer sheath (102) and distal sheath (106) and into body cavity (C), such that distal sheath (106) serves as an introducer cannula. Before, during, or after advancement of scope shaft (108), distal sheath (106) may be articulated by the drive mechanism to a desired articulated state. Additionally, upon exiting distal sheath (106) and entering body cavity (C), articulation section (112) of scope shaft (108) may be driven by the drive mechanism to orient distal tip section (114) in a desired direction. Additionally, distal tip section (114) may be rotated relative to the proximal remainder of scope shaft (108) to provide desired visualization within body cavity (C).

III. Example of a Surgical Cannula Having Distal Articulation Joint

As described above, distal sheath (106) of surgical scope (100) may be configured to articulate in one or more planes to facilitate positioning of distal tip section (114) within body cavity (C) for optimal visualization of a target surgical site and surrounding anatomical structures. In some instances, it may be desirable to combine a deflectable surgical scope with a surgical cannula having a distal articulation feature in the form of an articulation joint. As described below, FIGS. 8-21 show some versions of such surgical cannulas.

Figure 8:
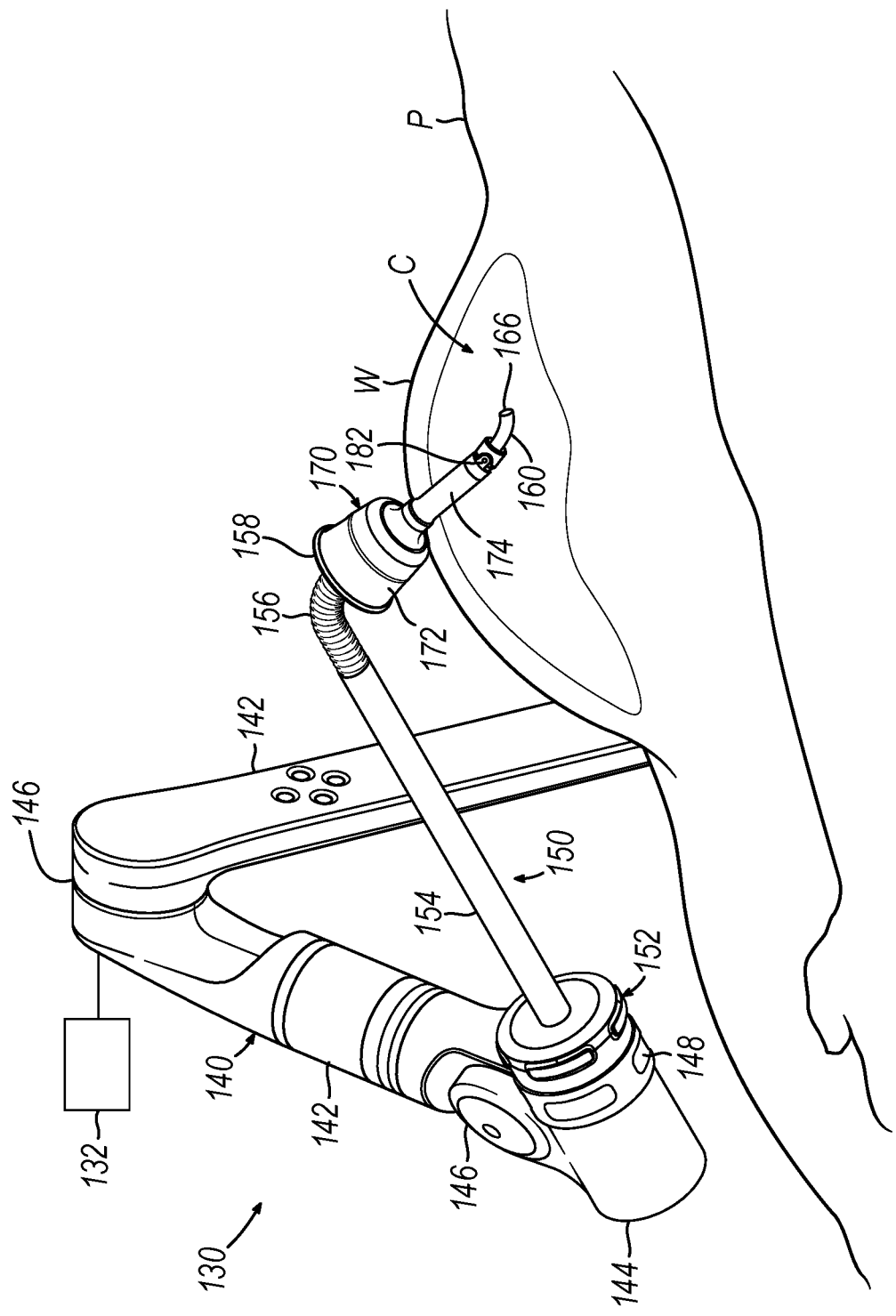
FIG. 8 depicts a perspective view of another example of a robotic system having a robotic arm, a surgical scope having a deflectable distal shaft portion, and a cannula having an articulation feature.

FIG. 8 shows an example of a robotic system (130) that includes a robotic arm (140), a surgical instrument in the form of a surgical scope (150) removably coupled to a head (144) of robotic arm (140), and a surgical access device in the form of a cannula (170) coupled with surgical scope (150) remotely from head (144). Robotic arm (140) includes arm segments (142) and head (144) that are interconnected by movable joints (146), where head (144) includes a motorized drive mechanism (148) that may be similar to instrument driver (66) described above. Robotic arm (140) is operable to selectively position and orient surgical scope (150) relative to a patient (P) by driving arm segments (142) and drive mechanism (148) based on control signals received from a master controller (132) of robotic system (130), shown schematically. Master controller (132) may be operatively coupled with robotic arm (140), including surgical scope (150), via a wired connection or a wireless connection, for example.

Robotic arm (140) may be similar in structure and function to any of robotic arms (20, 32) described above, and is mountable to any suitable arm support structure such as a column (22) or any of the other arm support structures disclosed above or in the patent references incorporated by reference herein. Though not shown, robotic system (130) may further include one or more additional robotic arms (140) each supporting and controlling a respective surgical instrument having an end effector of which surgical scope (150) may provide visualization within a body cavity (C) of the patient (P).

Figure 9:
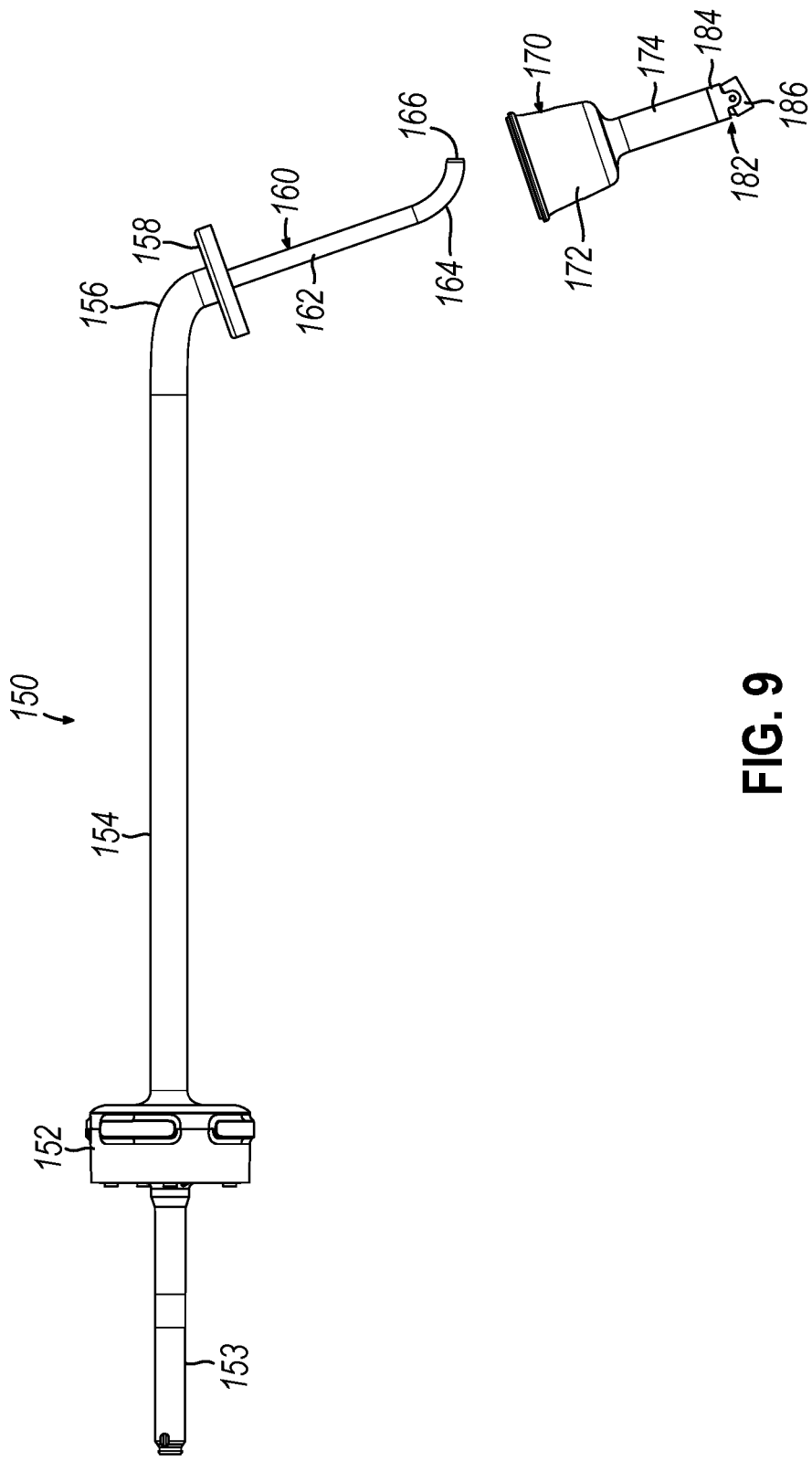
FIG. 9 depicts a schematic side elevational view of the surgical scope and the cannula of FIG. 8.
Figure 10:
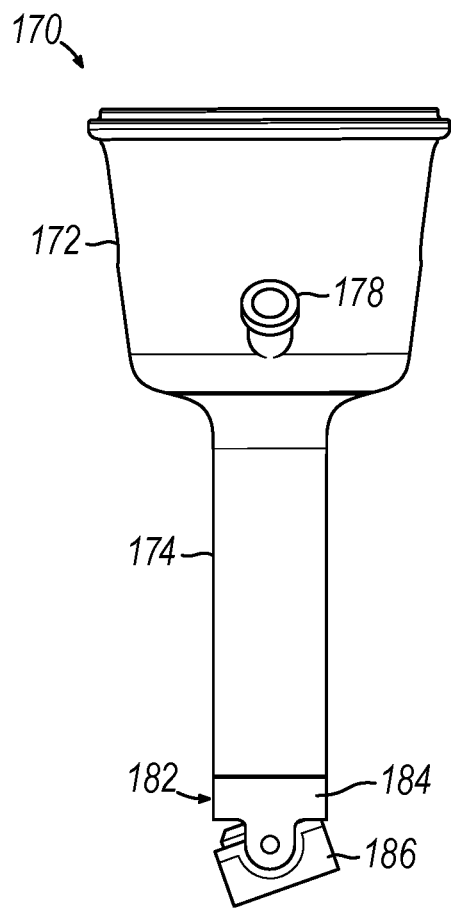
FIG. 10 depicts a side elevational view of the cannula of FIG. 8, showing the articulation feature in an articulated state.

As shown in FIGS. 8 and 9, surgical scope (150) includes a scope base (152), an elongate rigid outer sheath (154) that extends distally from scope base (152), a flexible joint (156) at a distal end of outer sheath (154), a cannula docking plate (158) at a distal end of flexible joint (156), and a scope shaft (160) slidably disposed within outer sheath (154). Flexible joint (156) may have a predefined curved shape or be configured to assume a curved shape as shown and may include an internal sheath (not shown) that resists binding. Similar to scope shaft (108) described above, scope shaft (160) includes a deflectable distal shaft portion (162) that includes an articulation section (164). Scope base (152) may be similar to instrument base (76) described above in that scope base (152) is configured to attach to drive mechanism (148) of robotic arm head (144) such that drive inputs of scope base (152) operatively couple with respective drive outputs of drive mechanism (148). Scope base (152) includes an elongate cylindrical extension (153) (also referred to as a nosecone) that extends coaxially through a central clearance bore (not shown) of drive mechanism (148). Drive mechanism (148) is operable to drive insertion (i.e., longitudinal advancement and retraction) and articulation of scope shaft (160) relative to outer sheath (154). In some versions, drive mechanism (148) may also be further operable to drive articulation of cannula (170), described below.

As shown in FIGS. 8-11, cannula (170) includes a proximal structure in the form of a cup (172) having an open proximal end, and a distal structure in the form of an elongate tube (174) that extends distally from a distal end of cup (172) and has a smaller maximum outer diameter than cup (172). A distal end of cup (172) tapers radially inwardly to the proximal end of tube (174). In the present version, both of cup (172) and tube (174) are rigid such that neither is configured to deflect laterally during use when tube (174) is deployed in a body wall (W). In other versions, all or a portion of tube (174) may be laterally deflectable (e.g., flexible).

Figure 11:
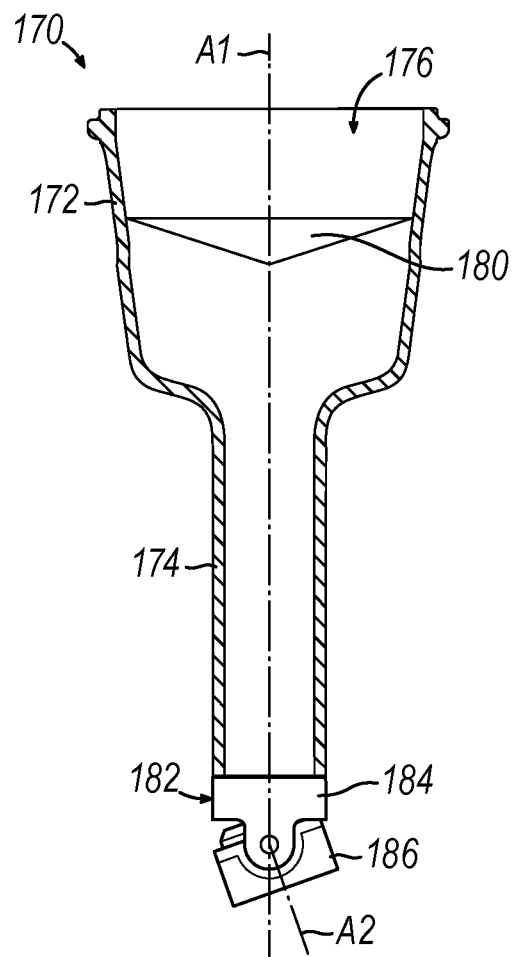
FIG. 11 depicts a side cross-sectional view of the cannula of FIG. 8 with the articulation feature in an articulated state.

As shown in FIG. 11, the interiors of cup (172) and tube (174) cooperate to define a working channel (176) that extends along a central primary axis (A1) of cannula (170) and is sized and configured to receive and guide scope shaft (160) of surgical scope (150) longitudinally therethrough into body cavity (C). A proximal lip of cup (172) is configured to releasably couple with cannula docking plate (158) of surgical scope (150) such that the open proximal end of cup (172) is enclosed by docking plate (158). A distal portion of an annular sidewall of cup (172) includes an access port (178) that communicates with working channel (176). In some versions, access port (178) may be configured to couple with a source of insufflation gas, such as pressurized air, for directing the gas into or out of body cavity (C) to regulate insufflation of body cavity (C). Additionally, or alternatively, access port (178) may be configured to receive various other fluids and/or surgical instruments. Cup (172) further includes an inner seal member (180) (shown schematically) configured to establish an air-tight seal against scope shaft (160) when scope shaft (160) is positioned within working channel (176), and also when scope shaft (160) is removed from working channel (176), to thereby maintain insufflation of body cavity (C) during a procedure. In other versions, cannula (170) and/or surgical scope (150) may include one or more additional seal members configured to maintain insufflation of body cavity (C).

In addition to the foregoing, cannula (170) may be constructed and operable in accordance with at least some of the teachings of U.S. Pat. No. 10,792,069, entitled "Trocar Seal Assemblies," issued Oct. 6, 2020; U.S. Pat. No. 10,820,924, entitled "Asymmetric Shaft Seal," issued Nov. 3, 2020; U.S. Pub. No. 2021/0338272, entitled "Pinch to Release Cannula Depth Limiter," published Nov. 4, 2021, issued as U.S. Pat. No. 11,633,211 on Apr. 25, 2023; and/or U.S. Pat. No.

10,939,937, entitled "Trocar with Oblique Needle Insertion Portion and Perpendicular Seal Latch," issued Mar. 9, 2021. The disclosures of these references are incorporated by reference herein, in their entirety.

Cannula (170) further includes an articulation feature in the form of an articulation joint (182) at the distal end of tube (174). Similar to distal sheath (106) of surgical scope (100), articulation joint (182) is configured to facilitate in positioning a distal tip section (166) of surgical scope shaft (160) at a desired location and orientation within body cavity (C) to visualize the target surgical site. Articulation joint (182) of the present example includes a rigid proximal link (184) that is affixed to a distal end of tube (174), and a rigid distal link (186) pivotably coupled with proximal link (184) about a pivot axis that extends transversely to primary axis (A1) of cannula (170). Accordingly, articulation joint (182) of the present version is configured to articulate in a single plane that includes primary axis (A1) to orient distal link (186) along an articulated secondary axis (A2) that is angled relative to primary axis (A1), as shown in FIG. 11. In other versions, distal link (186) may be configured to pivot relative to proximal link (184) about one or more additional pivot axes, and/or articulation joint (182) may include one or more additional links pivotably coupled with proximal and distal links (184, 186) about non-parallel pivot axes, such that articulation joint (182) is configured to articulate in two or more planes that intersect one another and include or extend parallel to primary axis (A1).

Articulation of articulation joint (182) may be active or passive. For instance, articulation joint (182) may be driven by drive mechanism (148) of robotic arm head (144) via one or more articulation drivers (not shown), such as one or more tendons (e.g., pull-wires, drive bands, etc.); or by another drive mechanism positioned remotely from robotic arm head (144), for example as described below. Alternatively, articulation joint (182) may be configured to passively assume an articulated state in response to scope shaft (160) being driven into an articulated state at its articulation section (164). In some such versions, articulation joint (182) may be resiliently biased toward a straight configuration in which distal link (186) is coaxial with primary axis (A1) of cannula (170). In other versions, articulation joint (182) may be manipulated by hand into an articulated state before insertion through body wall (W), and it may be configured to maintain such a preset articulated state. As another variation, another instrument (e.g., grasper) within the cavity (C) may be used to manipulate articulation joint (182) in the patient (P).

Figure 12A:
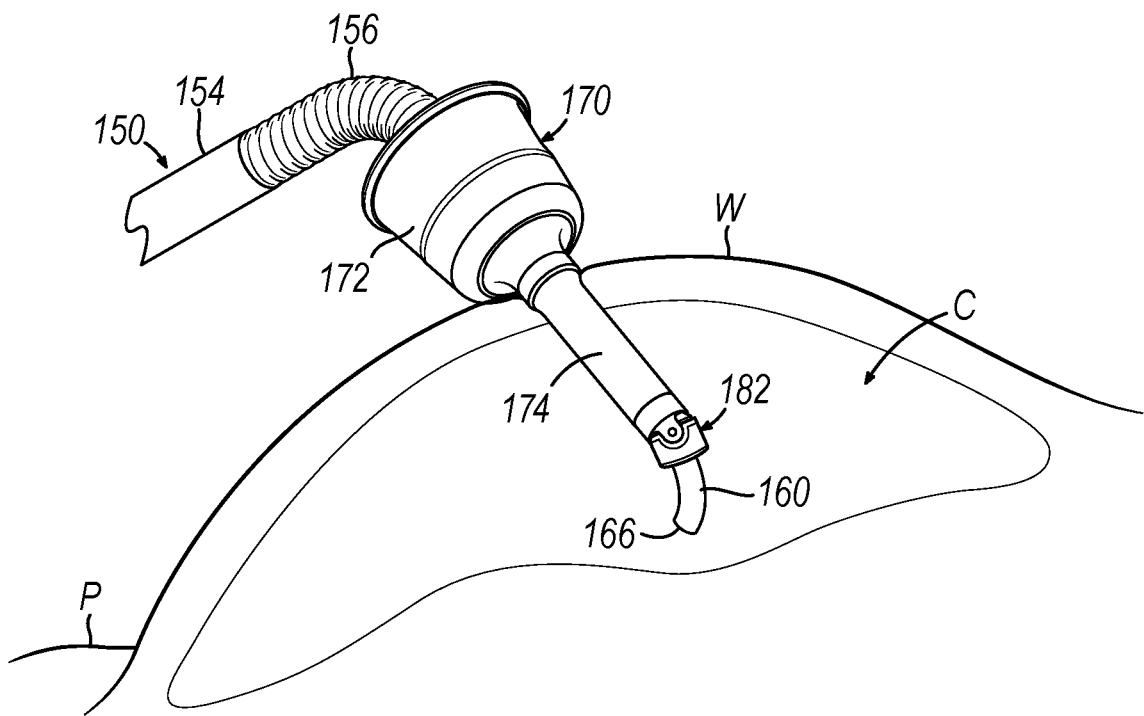
FIG. 12A depicts a perspective view of the surgical scope and the cannula of FIG. 8 inserted into the body cavity of a patient, showing the articulation feature in a first articulated state and the deflectable distal shaft portion in a first deflected state.

As shown in FIG. 12A, cannula tube (174) is inserted through body wall (W), for example using an obturator (not shown), such that at least the distal end of cannula tube (174) is positioned within body cavity (or "intracorporeally") and cup (172) is positioned external to body cavity (C) (or "extracorporeally"). In versions where an obturator is used during insertion through body wall (W), the obturator may be removed from cannula tube (174) before surgical scope shaft (160) is inserted through cannula tube (174). As shown in FIG. 8, robotic arm (140) and its head (144) are positioned remotely from cannula (170) such that outer sheath (154) drapes away from cannula (170) via the flexibility of flexible joint (156), thus generally clearing the workspace directly above body wall (W) for use by other robotic arms (not shown) supporting other surgical instruments. In some procedures, cannula (170) may be stabilized relative to the patient with a mechanical grounding feature (not shown), such as a stationary arm. Such a stationary arm may be secured to table (16, 34) or some other grounding structure.

Figure 12B:
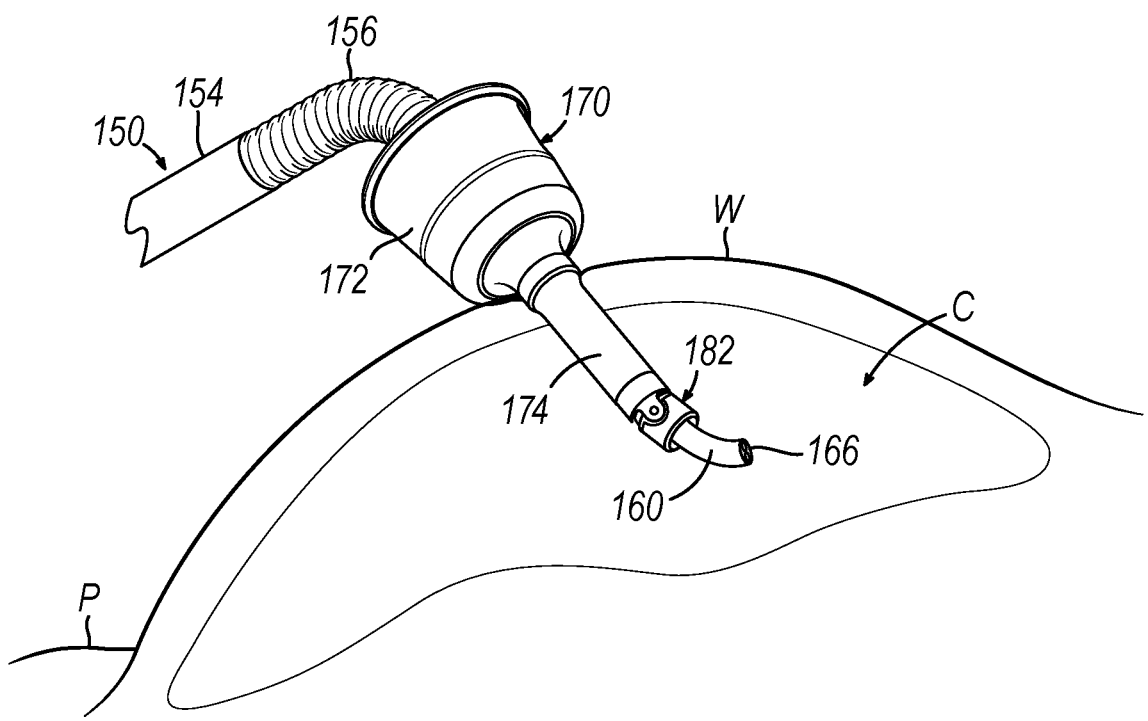
FIG. 12B depicts a perspective view of the surgical scope and the cannula of FIG. 12A, showing the articulation feature in a second articulated state and the deflectable distal shaft portion in a second deflected state.
Figure 12C:
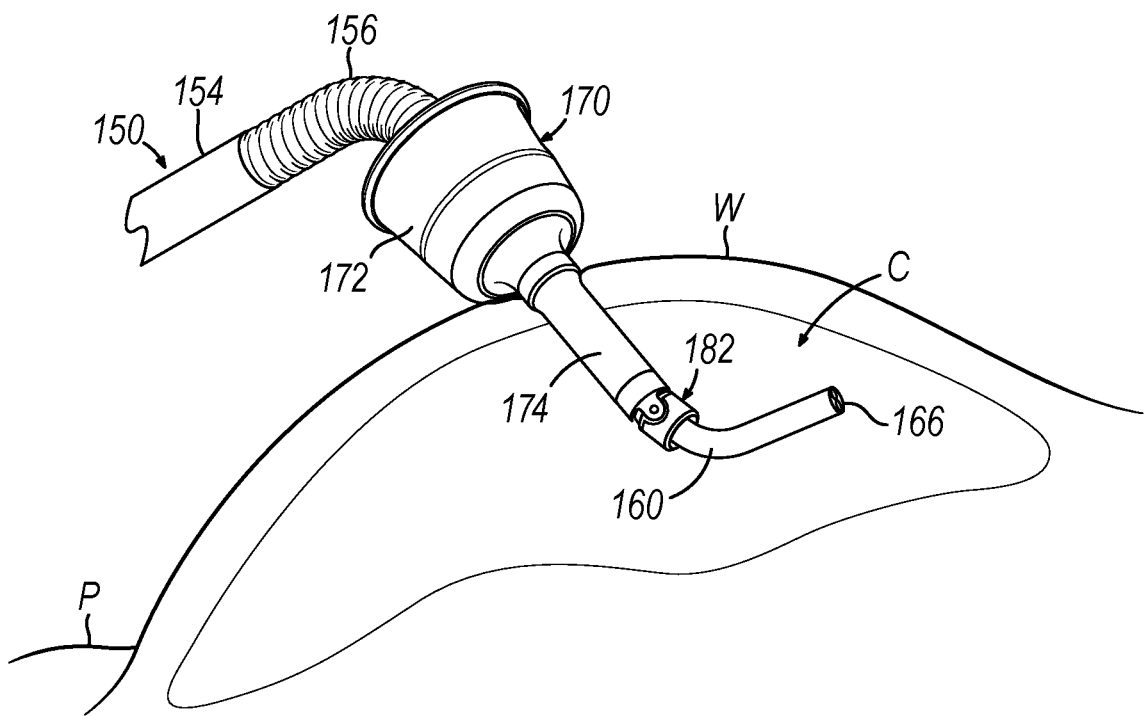
FIG. 12C depicts a perspective view of the surgical scope and the cannula of FIG. 12A, showing the deflectable distal shaft portion inserted further into the body cavity.
Figure 12D:
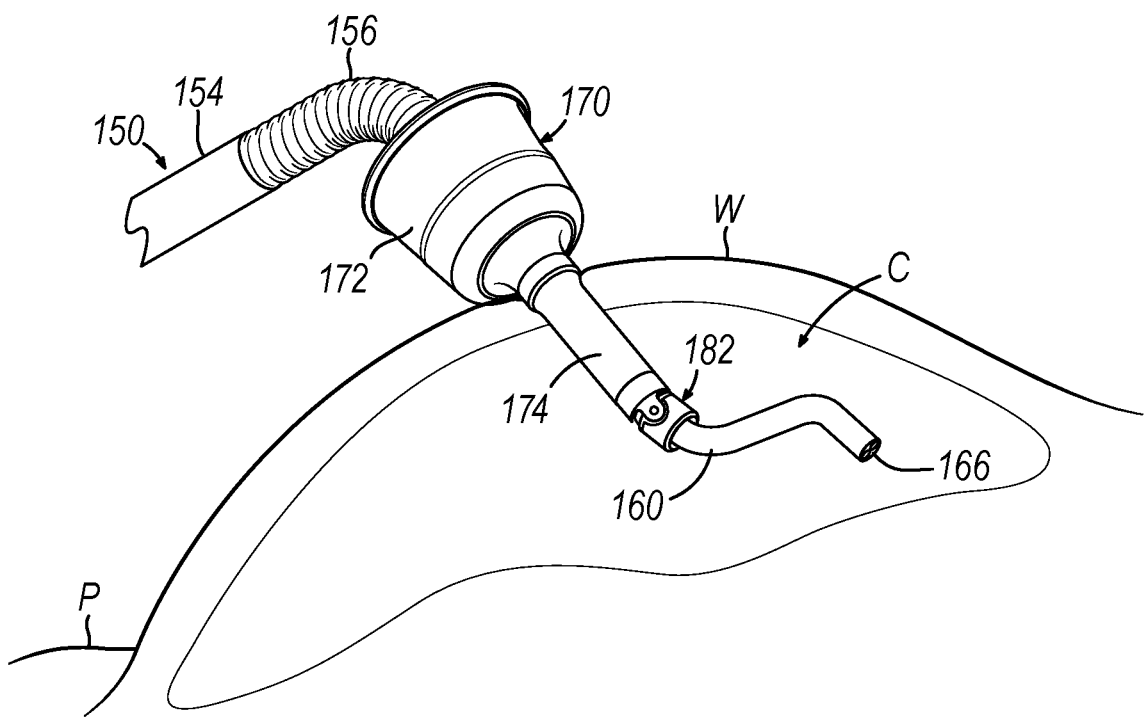
FIG. 12D depicts a perspective view of the surgical scope and the cannula of FIG. 12A, showing a distal end of the deflectable distal shaft portion in an articulated state.

As shown in FIGS. 12A-12D, scope shaft (160) is actuated by drive mechanism (148) distally through cannula (170) and into body cavity (C). FIG. 12A shows articulation joint (182) in a first example of an articulated state in which articulation joint (182) directs scope shaft (160) in a first angled direction within body cavity (C). FIG. 12B shows articulation joint (182) in a second example of an articulated state in which articulation joint (182) directs deflectable scope shaft (160) in a second angled direction within body cavity. As noted above, articulation joint (182) may be configured to transition between such articulated states actively or passively. In cases of active cannula articulation, deflectable distal shaft portion (162) may be flexible along its length to conform to the curvature defined by articulation joint (182) as scope shaft (160) is inserted further into body cavity (C), as shown particularly in FIG. 12C. As shown in FIG. 12D, scope shaft (160) may be articulated at its distal articulation section (164) to suitably orient its distal tip section (166) within body cavity (C) to provide visualization of the target surgical site and/or surrounding anatomical structures. In the example shown in FIG. 12D, scope shaft (160) has achieved a dogleg bend configuration, though scope shaft (160) may alternatively achieve any other suitable kind of articulated state, including but not limited to different articulated states with two or more bends regions at different corresponding positions along the length of scope shaft (160).

IV. Example of a Surgical Scope with Resilient Outer Sheath

Figure 13A:
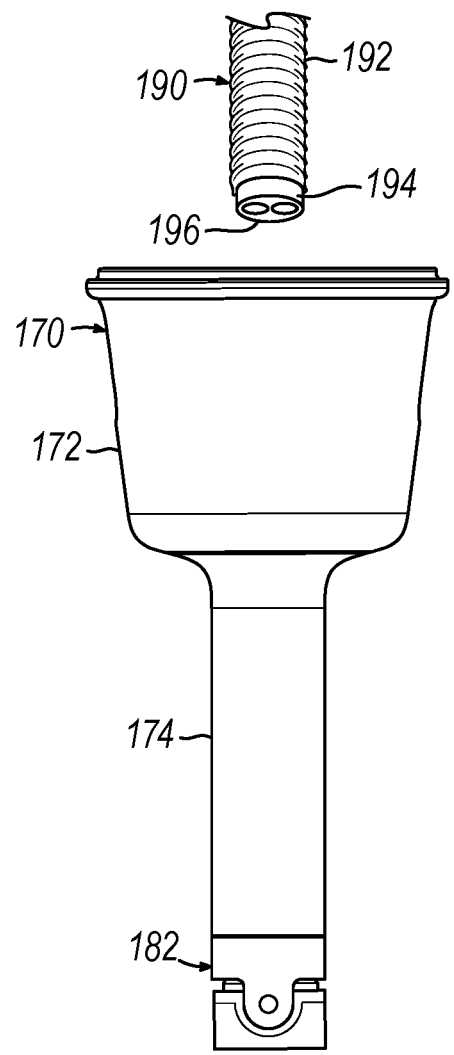
FIG. 13A depicts a side elevational view of the cannula of FIG. 8 in combination with another example of a surgical scope having a deflectable distal shaft portion that includes a resilient sheath, showing the deflectable distal shaft portion in a straight configuration before insertion through the cannula.
Figure 13B:
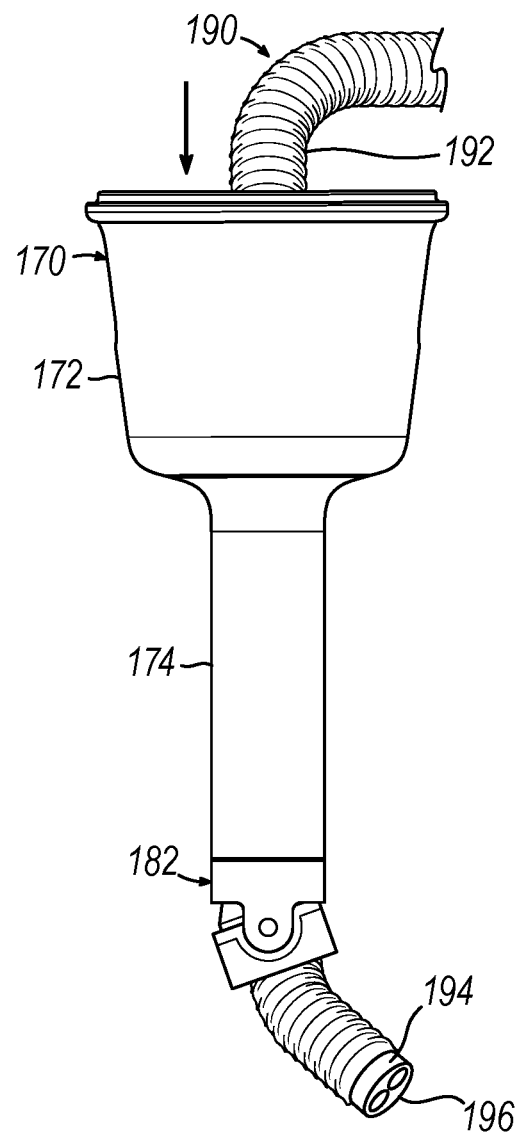
FIG. 13B depicts a side elevational view of the cannula and the surgical scope of FIG. 13A, showing a portion of the deflectable distal shaft portion in a flexed configuration while advancing through the cannula.
Figure 13C:
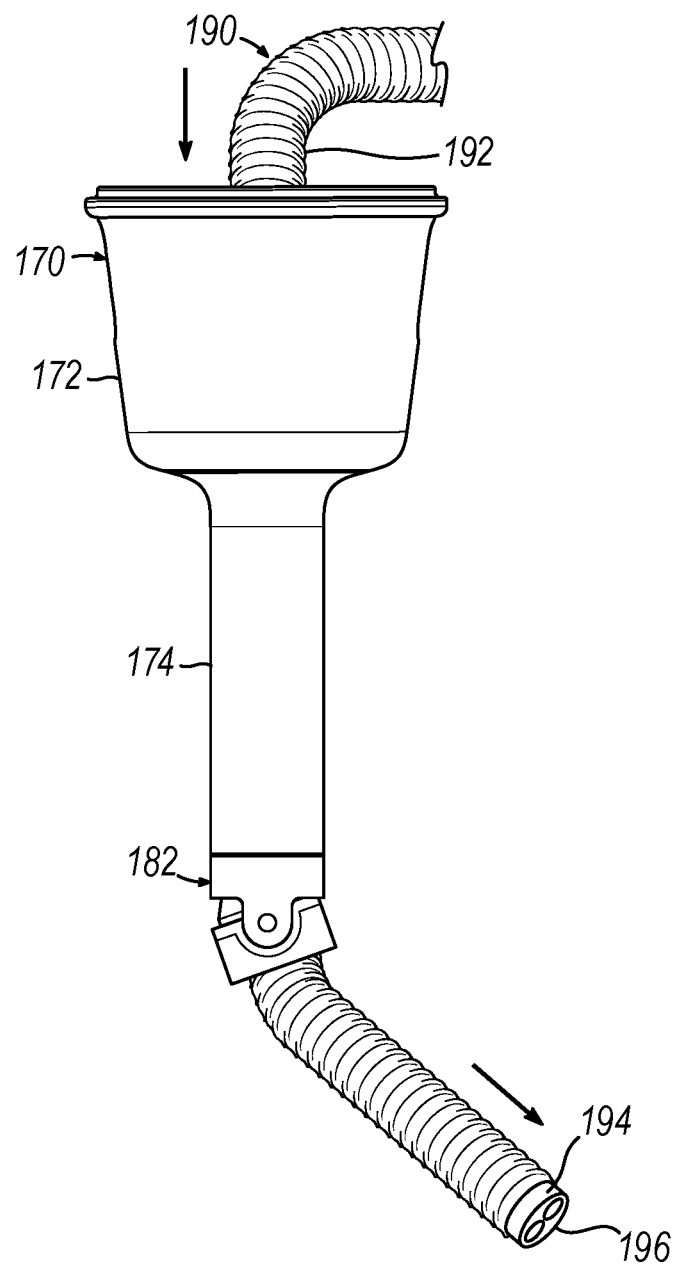
FIG. 13C depicts a side elevational view of the cannula and the surgical scope of FIG. 13A, showing a distal end of the deflectable distal shaft portion resuming a straight configuration distal to the cannula.

In some instances, it may be desirable to provide a surgical scope that includes a scope shaft having at least a portion that is resiliently biased toward a straight configuration and is configured to passively deflect by flexing away from the straight configuration. FIGS. 13A-13C show cannula (170) in combination with an example of an alternative surgical scope shaft (190) that exhibits such functionality. Scope shaft (190) may be integrated with any of the examples of surgical scopes disclosed here. Scope shaft (190) includes a resilient outer sheath (192) shown in the form of a coil spring pipe, which may be similar in construction to an extension or compression coil spring, and a core (not shown) that is encircled by resilient outer sheath (192) and may be similar in construction to scope shaft (190) described above. For instance, scope shaft (190) may include a drivable articulation section. Scope shaft (190) further includes a distal tip section (194) that includes an optical module having a lens (196) that provides visualization of a target surgical site with a body cavity.

As shown in FIG. 13A, resilient outer sheath (192) biases scope shaft (190) toward a straight configuration when no lateral forces are acting on scope shaft (190), such that scope shaft (190) is self-straightening. As shown in FIGS. 13B-13C, when articulation joint (182) of cannula (170) is in an articulated state, scope shaft (190) resiliently deflects (i.e., flexes) laterally to conform to the angled configuration of articulation joint (182) as scope shaft (190) extends distally through articulation joint (182). Scope shaft (190) may also flex during distal insertion at a location proximal to cannula cup (172) if a scope base (not shown) is positioned laterally offset from cannula (170) or scope shaft (190) is otherwise directed into cup (172) along an axis that is non-coaxial with cannula (170). As a portion of scope shaft (190) extends distally beyond the articulated articulation joint (182), that portion of scope shaft (190) resiliently returns to its straight configuration. This distal region of scope shaft (190) may remain straight as scope shaft (190) continues to advance distally relative to articulation joint (182), with the bend in scope shaft (190) being maintained at articulation joint (182).

V. Example of a Surgical Cannula with Flexible Tube

Figure 14:
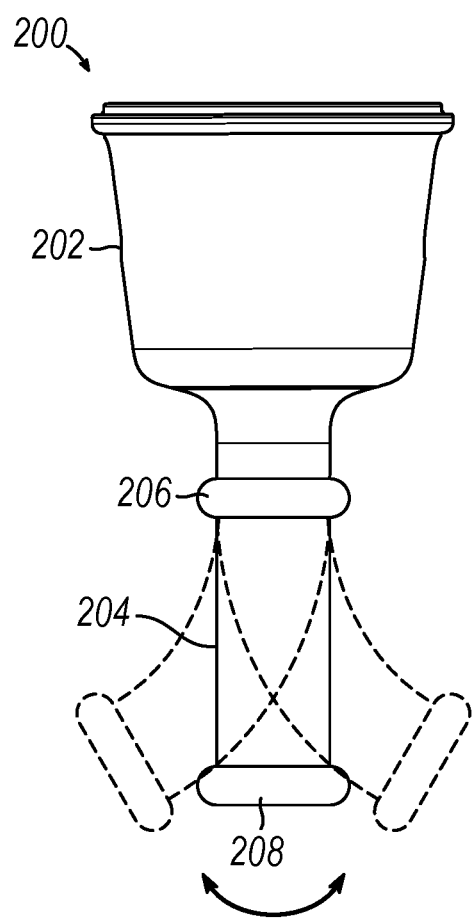
FIG. 14 depicts a side elevational view of another example of a cannula having a flexible tube.

FIG. 14 shows an example of an alternative cannula (200) that includes a cup (202) similar to cup (172), and a tube (204) extending distally from cup (202). Tube (204) is elastically deformable along its length and includes a proximal annular rib (206) at or near the junction with cup (202), and a distal annular rib (208) at or near the distal end of tube (204). Annular ribs (206, 208) may be formed integrally with tube (204) or otherwise be fixed or fixable axially relative to tube (204). Annular ribs (206, 208) are configured to abut respective proximal and distal surfaces of a body wall of a patient and thereby cooperate to longitudinally stabilize tube (204) at a predetermined depth relative to the body wall. Accordingly, cannula (200) tube may be similar in structure and function to a thoracic wound protector. The flexibility of tube (204) may nevertheless accommodate different lateral bend angles, which may thereby accommodate articulation or other bending within a shaft of a scope that is disposed in tube (204). While tube (204) is shown as distally terminating at distal annular rib (208) in this example, some other versions may include a further distal region of tube (204) that extends distally past distal annular rib (208).

VI. Example of a Surgical Scope with Integrated Cannula

As described above in connection with FIGS. 8-13C, cannula (170) and surgical scopes (150) are independent structures, where cannula (170) is configured to guide scope shaft (160) of surgical scope (150) relative to a patient. In some instances, it may be desirable to integrate a cannula into the structure of a surgical scope, as well as provide the cannula with an articulation feature. FIGS. 15-22 show some versions of such configurations, as described in greater detail below.

A. Surgical Scope with Integrated Cannula Having Articulation

Figure 15:
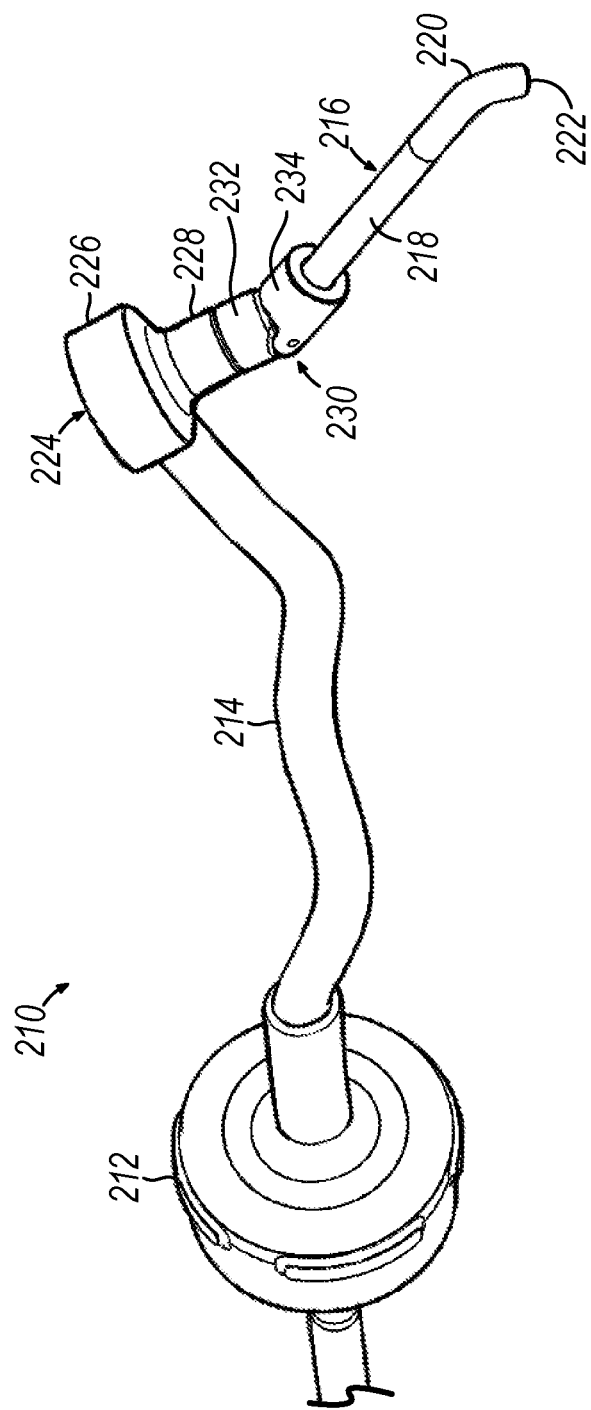
FIG. 15 depicts a perspective view of another example of a surgical scope having an integrated cannula with an articulation feature.
Figure 16:
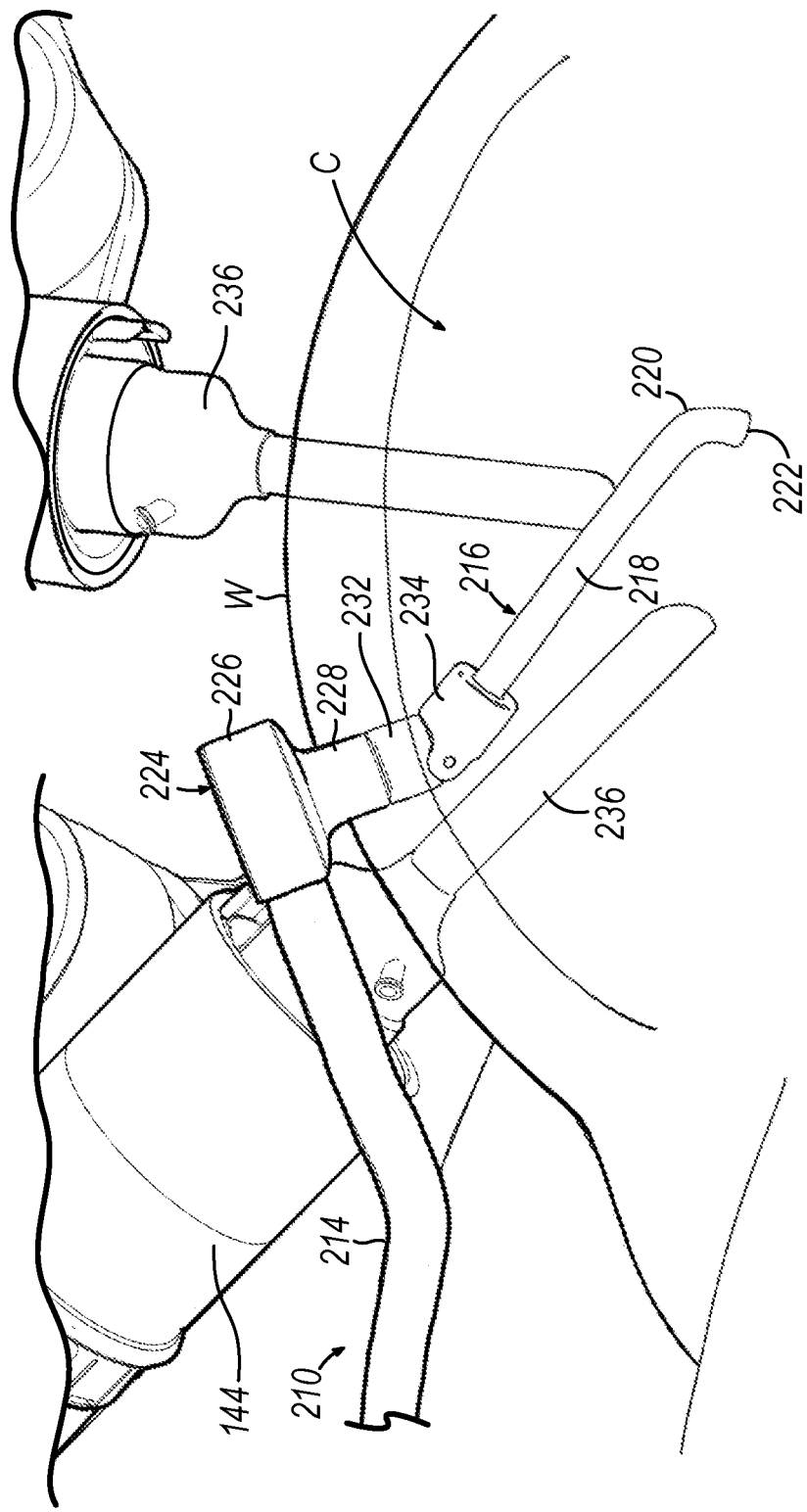
FIG. 16 depicts a perspective view of an example of a robotic system that incorporates the surgical scope of FIG. 15.

FIGS. 15-16 shows an example of a surgical scope (210) having a scope base (212), an outer sheath (214) extending distally from scope base (212), a scope shaft (216) slidably disposed within outer sheath (214), and a cannula (224) affixed to a distal end of outer sheath (214). Scope base (212) may be similar in structure and function to scope base (152) described above and is configured to removably couple to a robotic arm head, such as robotic arm head (144). Outer sheath (214) of the present version is flexible though may be rigid in other versions. In some versions, outer sheath (214) may include a rigidizing feature such that outer sheath (214) is configured to selectively transition between a flexible state and a rigid state. In still other versions, outer sheath (214) is malleable. Scope shaft (216) is generally similar to scope shafts (108, 160) and includes a deflectable distal shaft portion (218) that includes an articulation section (220), and a distal tip section (222) that includes an optical module having a lens (not shown) operable to provide visualization of a target surgical site with the body cavity (C) of a patient (P). Surgical scope (210) may be stabilized (or "grounded") relative to a patient in any suitable manner, such as by use of a separate stabilizing arm or by releasable attachment (e.g., adhesive attachment) to one or more body portions of the patient. Alternatively, table (16, 34) or some other structure may be used to mechanically ground surgical scope (210).

Cannula (224) includes a proximal structure in the form of a puck-shaped hub (226) having a closed proximal end, and a distal structure in the form of a tube (228) that extends distally from a distal end of hub (226). The distal end of hub (226) tapers radially inwardly to the proximal end of tube (228), where tube (228) has a smaller maximum outer diameter than hub (226). The interiors of hub (226) and tube (228) cooperate to define a working channel (not shown) that may be similar to working channel (176) and is sized and configured to slidably receive and guide scope shaft (216) longitudinally therethrough. Outer sheath (214) is affixed to a sidewall of hub (226) and communicates with the working channel such that outer sheath (214) is configured to direct scope shaft (216) into the working channel along an introductory axis that is angled (e.g., perpendicular) relative to the central primary axis of cannula (224). Hub (226) may include one or more internal guide features configured to guide scope shaft (216) along the transition from outer sheath (214) to cannula tube (228). As shown in FIG. 16, such a configuration provides the interface between outer sheath (214) and hub (226) with a minimal vertical footprint in the workspace above the patient (P). In other words, such a configuration may enable scope base (212) to be positioned by robotic arm head (144) such that hub (226) and at least a distal portion of outer sheath (214) lie within a plane positioned at a minimal height above body wall (W), and such that scope base (212) and robotic arm head (144) may be positioned at or beneath such plane.

Cannula (224) further includes an articulation joint (230) at the distal end of tube (228) that includes a rigid proximal link (232) affixed to the distal end of tube (228), and a rigid distal link (234) pivotably coupled with proximal link (232) about a pivot axis that extends transversely to a primary central axis of cannula (224). Accordingly, articulation joint (230) of the present version is configured to articulate in a single plane, though may be modified to articulate in multiple planes. Additionally, articulation of articulation joint (230) may be active or passive. In cases of active articulation, articulation joint (182) may be driven by drive mechanism (148) of robotic arm head (144), or by another drive mechanism positioned remotely from robotic arm head (144), such as a drive mechanism that is housed within hub (226) and includes one or more motors, for example. Articulation drive may be communicated to articulation joint (230) by one or more tendons (e.g., pull-wires, drive bands, etc.) and/or by any other suitable kind of actuation features.

As shown in FIG. 16, scope base (212) and the robotic arm head (144) to which it is coupled may be positioned remotely from the location at which cannula (224) extends through a body wall (W) of the patient (P), where cannula (224) is separated from the corresponding robotic arm head (144) by outer sheath (214). Advantageously, this may tend to create additional room in the workspace directly above body wall (W) to accommodate additional robotic arm heads (144), each of which may be coupled with a respective cannula (236) and control a respective surgical instrument (not shown) directed through the respective cannula (236). Additionally, articulation joint (230) of cannula (224) is configured to assume an articulated state as needed to direct deflectable distal shaft portion (218) and distal tip section (222) of scope shaft (216) along a desired trajectory so that distal tip section (222) may visualize a target surgical site within a body cavity (C) of the patient (P).

Figure 17:
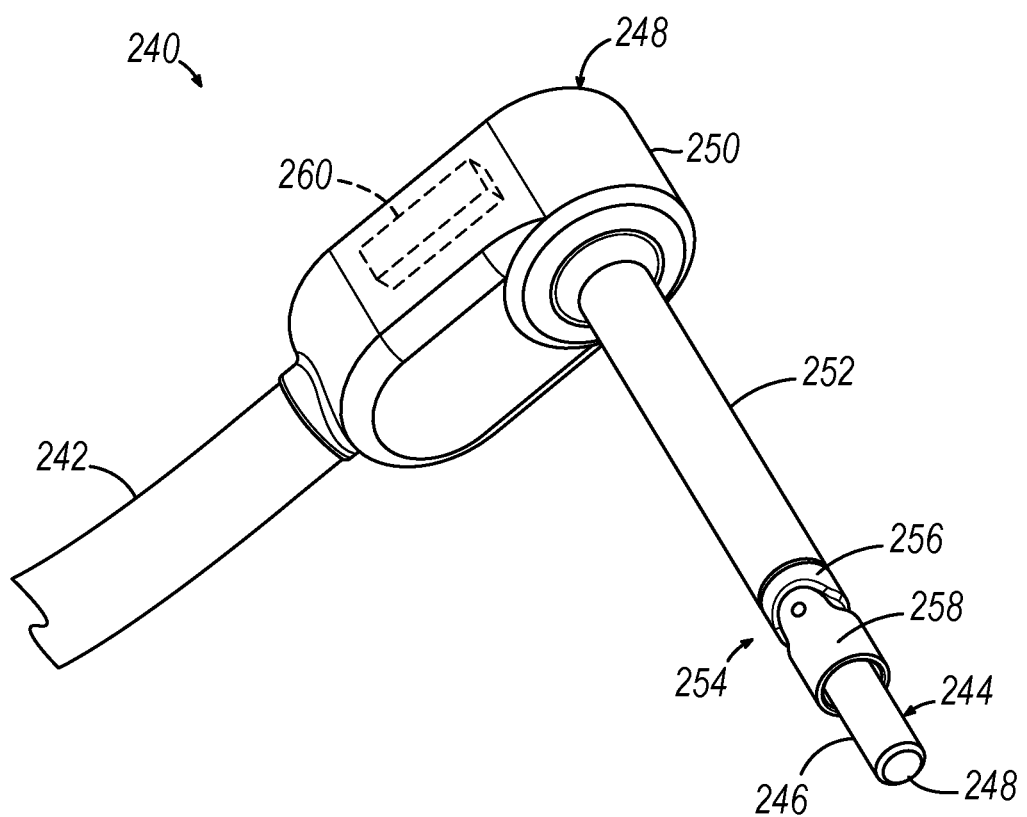
FIG. 17 depicts a perspective view of another example of a surgical scope having an integrated cannula with an articulation feature.

B. Examples of Surgical Scopes with Integrated Cannula Having Powered Articulation FIG. 17 shows another example of a surgical scope (240) that is similar to surgical scope (210) described above except as otherwise described below. Surgical scope (240) includes a scope base (not shown), an outer sheath (242) extending distally from the scope base, a scope shaft (244) slidably disposed within outer sheath (242), and a cannula (248) affixed to a distal end of outer sheath (242). Scope shaft (244) is generally similar to scope shafts (108, 160, 216) and includes a deflectable distal shaft portion (246) having an articulation section (not shown).

Cannula (248) includes a proximal structure in the form of an elongate, stadium-shaped hub (250), and a distal structure in the form of a tube (252) that extends distally from an underside of hub (250) at an elongate end opposite the end at which outer sheath (242) connects to hub (250). The interiors of hub (250) and tube (252) cooperate to define a working channel (not shown) that is sized and configured to slidably receive and guide scope shaft (244) longitudinally therethrough. Cannula (248) further includes an articulation joint (254) at the distal end of tube (252) that includes a rigid proximal link (256) and a rigid distal link (258) pivotably coupled about a pivot axis that extends transversely to a primary central axis of cannula (248).

Cannula hub (250) houses a motorized drive mechanism (260) (shown schematically) that includes one or motors and additional drive transmission components that may be similar to those of instrument driver (66) described above. Drive mechanism (260) is operable to drive articulation of articulation joint (254), for example by actuating one or more tendons or other articulation drivers (not shown) incorporated within cannula (248). In some versions, tube (252) may be rotatable relative to hub (250) about a longitudinal axis of tube (252) (i.e., a primary axis of cannula (248)), and in some such versions drive mechanism (260) may be operable to drive rotation of tube (252) relative to hub (250). In other versions, drive mechanism (260) may be operable to drive advancement and retraction of scope shaft (244) relative to cannula (248); and/or articulation of deflectable distal shaft portion (246) at its articulation joint.

Figure 18:
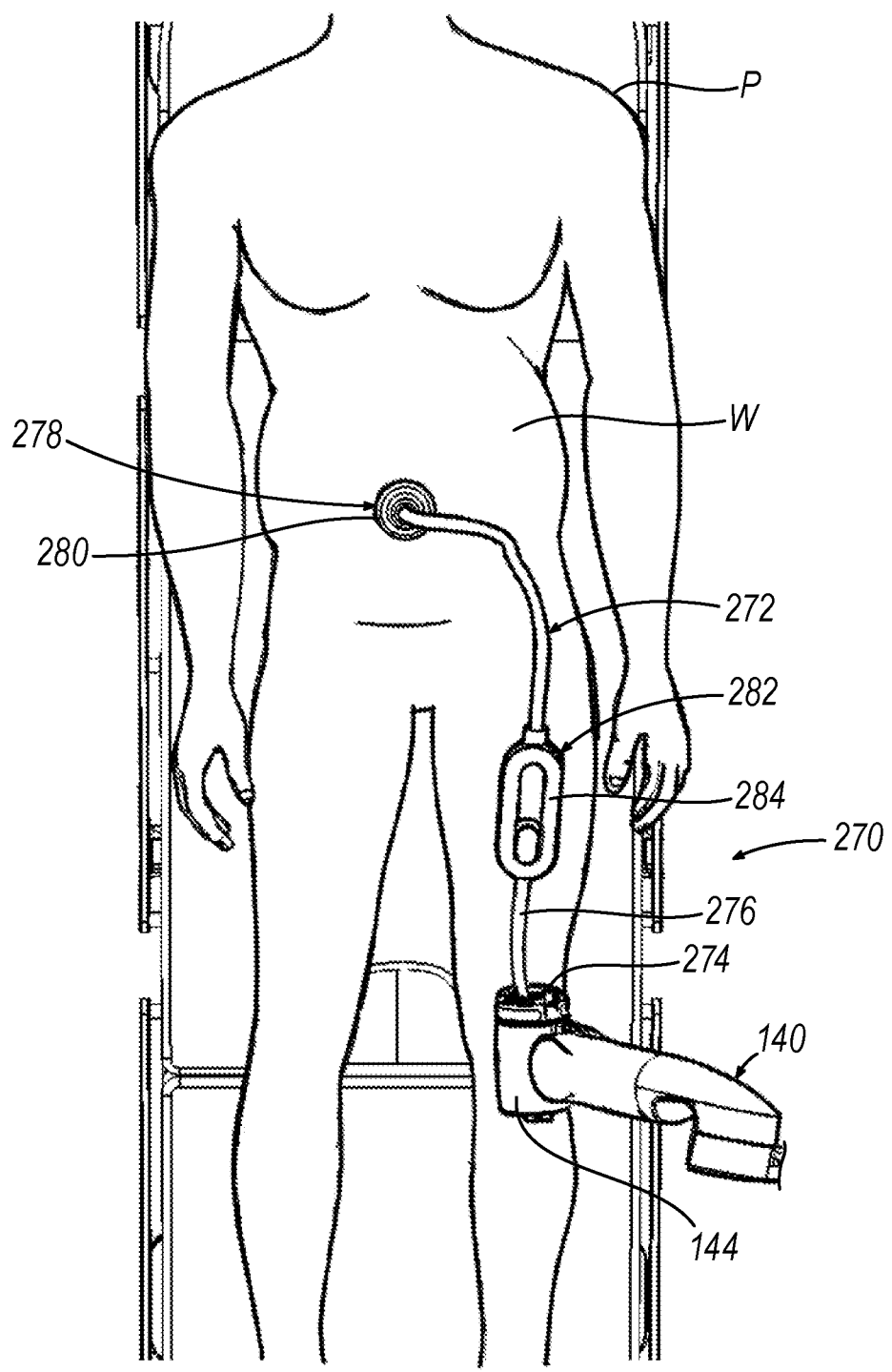
FIG. 18 depicts a top elevational view of a robotic system that incorporates a variation of the surgical scope of FIG. 17.

FIG. 18 shows another example of a robotic system (270) that includes robotic arm (140) and a surgical scope (272) removably coupled with robotic arm head (144). Surgical scope (272) includes a scope base (274), a flexible outer sheath (276) extending distally from scope base (274), a scope shaft (not shown) slidably disposed within outer sheath (276), an integrated cannula (278) affixed to a distal end of outer sheath (276), and a motorized drive mechanism (260) located between scope base (274) and cannula (278). Drive mechanism (260) may be similar to drive mechanism (260) in that drive mechanism (260) is configured to drive articulation of a tube (not shown) of cannula (278); rotation of the cannula tube relative to a hub (280) of cannula (278); advancement and retraction of the scope shaft relative to cannula (278) and outer sheath (276), and/or articulation of a deflectable distal shaft portion of the scope shaft of surgical scope (272). As shown, drive mechanism (260) includes a housing (284) that is distal to scope base (274) and proximal to cannula (278). In some versions, housing (284) may include one or more user input features (not shown), which may be configured to regulate the performance of drive mechanism (260). Additionally, each of cannula (278), outer sheath (276), and or drive mechanism housing (284) may be secured directly to patient (P) or otherwise stabilized relative to patient (P) with one or more suitable stabilizing features.

C. Examples of Surgical Scope Grounding Features

Figure 21:
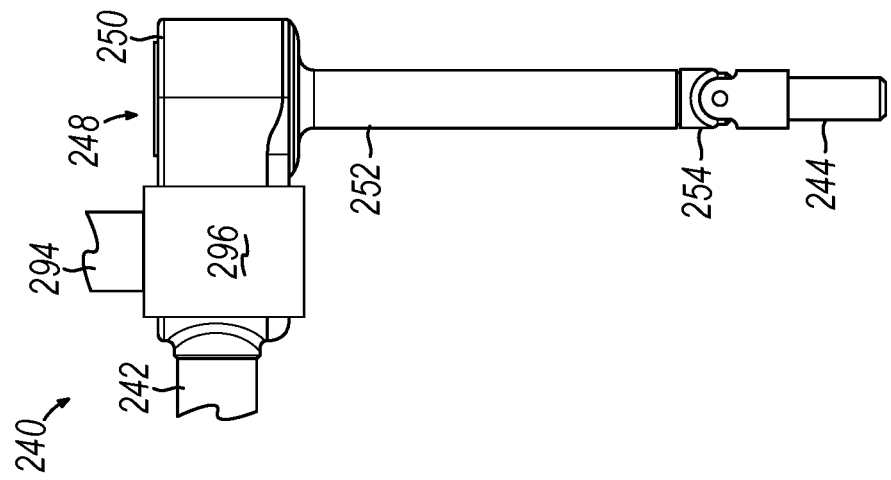
FIG. 21 depicts a side elevational view of the integrated cannula of the surgical scope of FIG. 17, shown in combination with a third example of a grounding feature, shown schematically.
Figure 20:
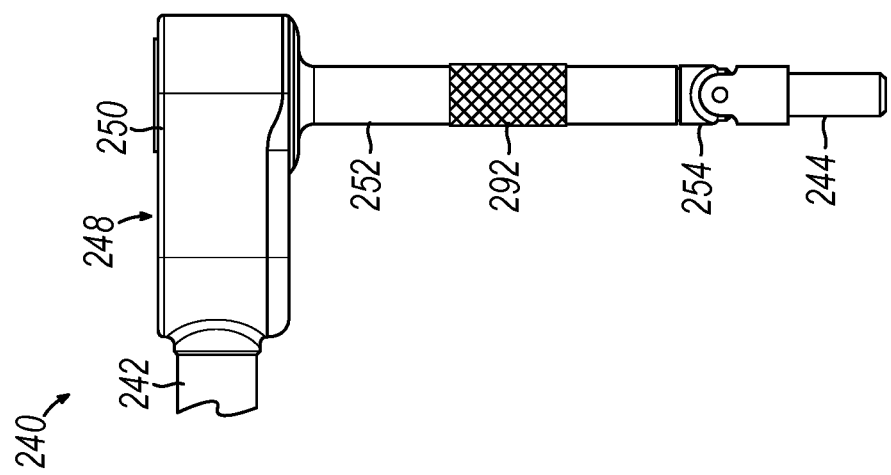
FIG. 20 depicts a side elevational view of the integrated cannula of the surgical scope of FIG. 17, shown with a second example of a grounding feature.
Figure 19:
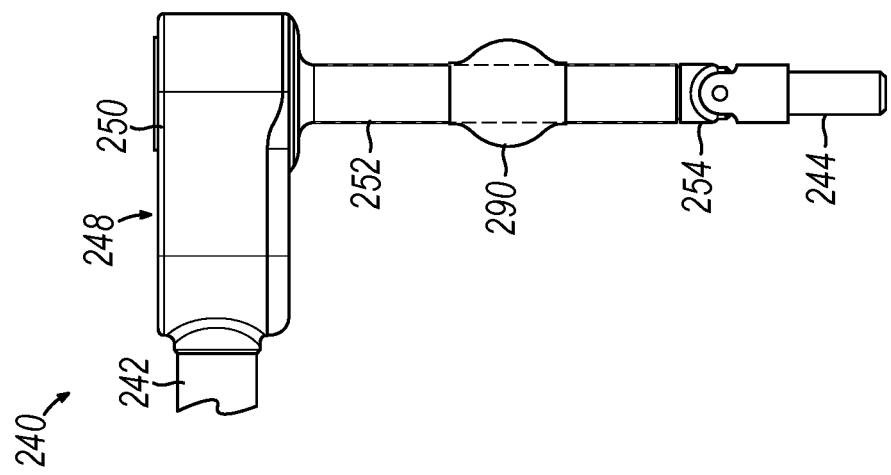
FIG. 19 depicts a side elevational view of the integrated cannula of the surgical scope of FIG. 17, shown with a first example of a grounding feature.

As described above, it may be desirable to stabilize a surgical scope of a robotic system relative to a patient using via one or more mechanical grounding features that are independent from the robotic arm (140). FIGS. 19-21 described below show examples of mechanical grounding features in connection with surgical scope (240), though these grounding features may also be used in connection with any of the other examples of surgical scopes disclosed herein.

FIG. 19 shows an example of a configuration in which surgical scope (240) includes a grounding feature in the form of an inflatable annular balloon (290) integrated into the cannula tube (252) of cannula (248). Balloon (290) encircles a medial portion of cannula tube (252) and is configured to transition from a deflated state (not shown) to the illustrated inflated state in response to balloon (290) being filled with an inflation fluid, which may be a liquid or a gas (e.g., air). In the inflated state, balloon (290) is configured to exert a radially outwardly directed force against, and thereby frictionally engage, the body wall (W) of the patient, thereby stabilizing cannula (248) and thus surgical scope (240) relative to the patient.

FIG. 20 shows another example of a configuration in which surgical scope (240) includes a grounding feature in the form of an adhesive element (292) that encircles a medial portion of cannula tube (252). In other versions, adhesive element (292) may be configured to couple outer sheath (242) of cannula (248) with a body portion of the patient, such as the abdomen.

FIG. 21 shows another example of a configuration in which surgical scope (240) includes a grounding feature in the form of a non-robotic arm (294) having a distal end (296) coupled (e.g., rigidly) with cannula hub (250). Though not shown, a proximal end of arm (294) may be secured to a stationary structure such as an operating table (16, 34) or an independent surgical cart, for example. In other versions, the distal end of arm (294) may be coupled to outer sheath (242) of surgical scope (240) in place of, or in addition to, being coupled to hub (250).

D. Example of a Port for Use with Surgical Scope Cannula

Any of the examples of cannulas described herein may be inserted directly through the body wall (W) of a patient (P) to access a body cavity (C), and they may include one or more inner seals that assist in maintaining insufflation of the body cavity (C) during a surgical procedure, for example while the corresponding scope shaft is slidably advanced and retracted through the cannula.

Figure 22:
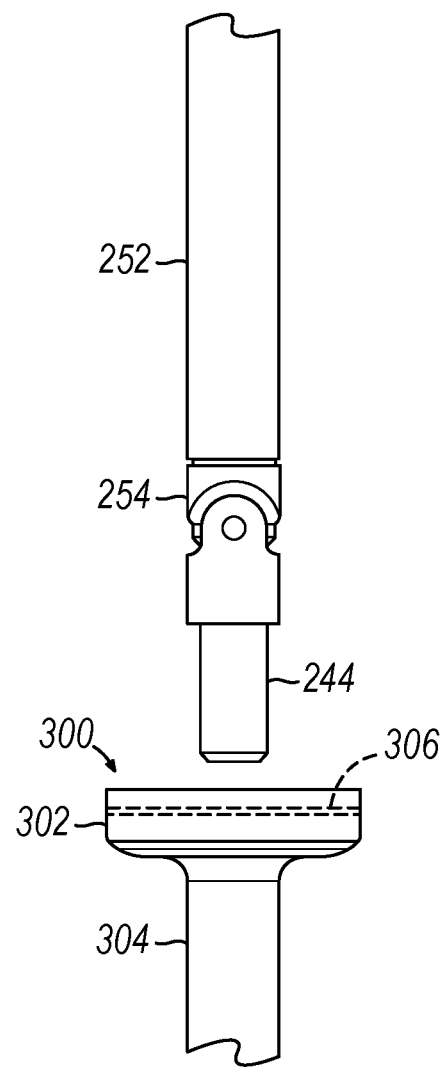
FIG. 22 depicts a side elevational view of a portion of the integrated cannula of FIG. 17, shown in combination with an example of a surgical port.

FIG. 22 shows an example of an alternative configuration in which cannula (248) is used in combination with a dedicated access device (300). Access device (300) is configured to serve as a secondary cannula and includes a cup (302) and a tube (304) that extends distally from cup (302) along a longitudinal axis and defines a working channel sized and configured to slidably receive cannula tube (252). Cup (302) includes an inner seal member (306) that may be similar to inner seal member (180) described above and is configured to maintain an air-tight seal both in the presence of cannula tube (252) and in the absence of cannula tube (252) to maintain insufflation of the body cavity. Accordingly, use of access device (300) may enable cannula (248) to be removed from the body wall during a procedure, for example to clean the distal tip of scope shaft (244), while maintaining insufflation of the body cavity.

VII. Example of a Surgical Cannula Having Rotatable Angled Tip

Figure 23:
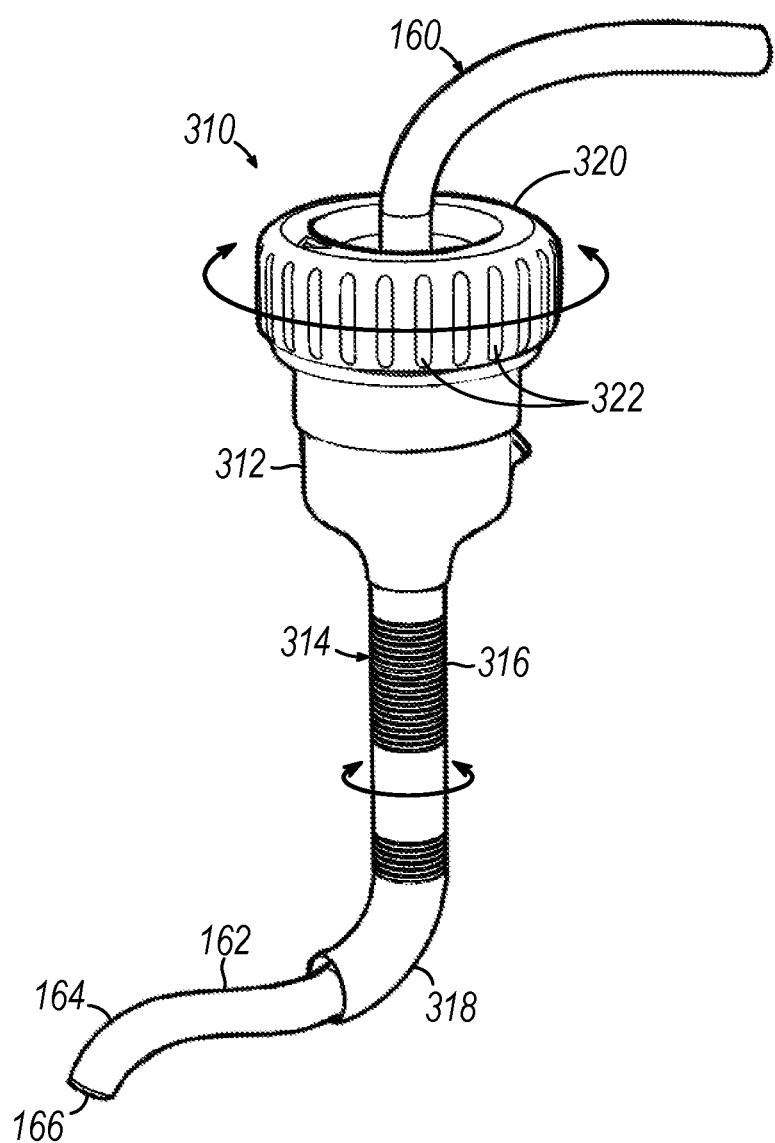
FIG. 23 depicts a perspective view of an example of a cannula having an angled distal tip and a tip actuator, shown in combination with a deflectable shaft portion of a surgical scope.
Figure 24:
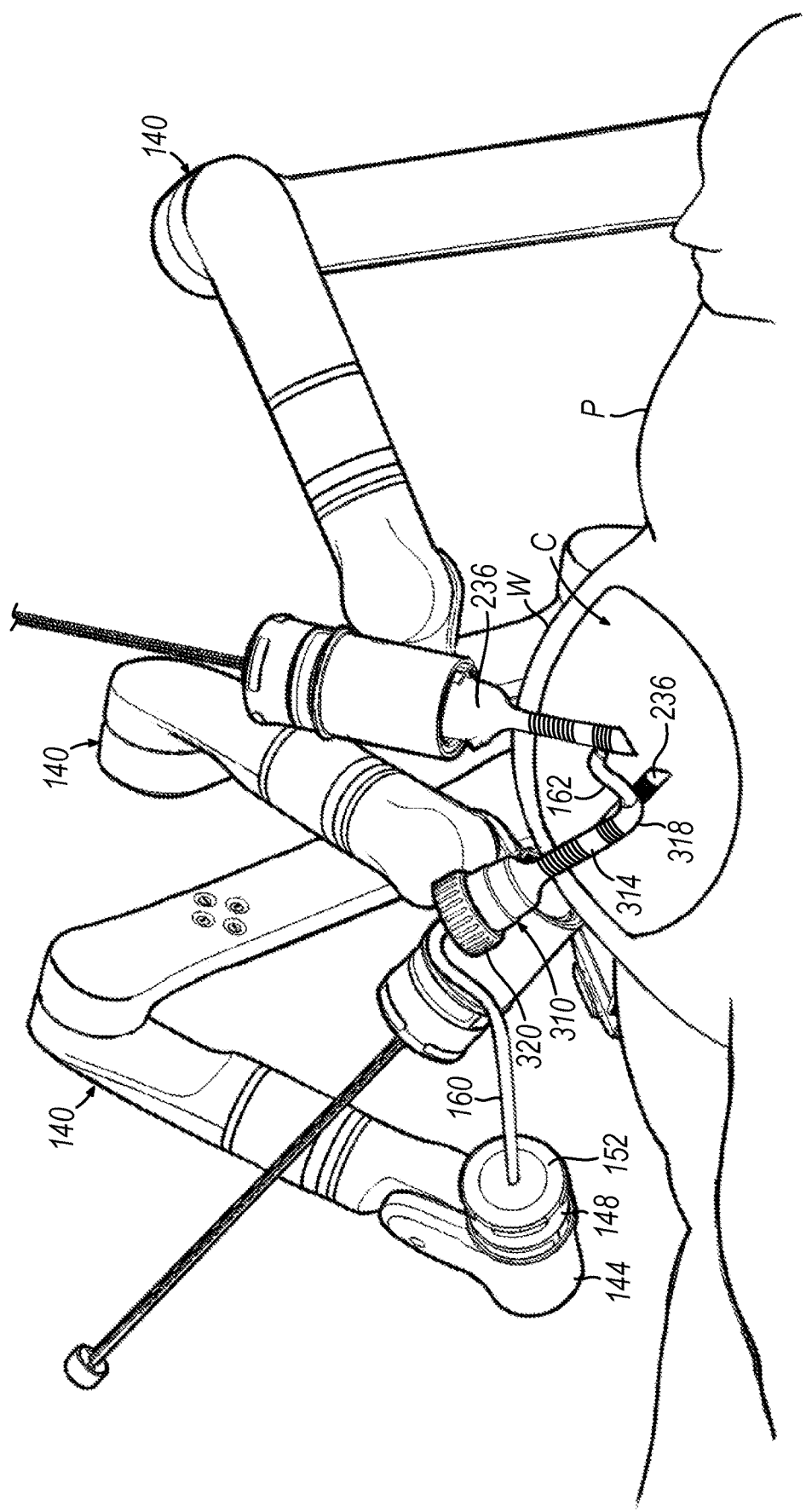
FIG. 24 depicts a perspective view of an example of a robotic system that incorporates the cannula and surgical scope of FIG. 23.
Figure 25:
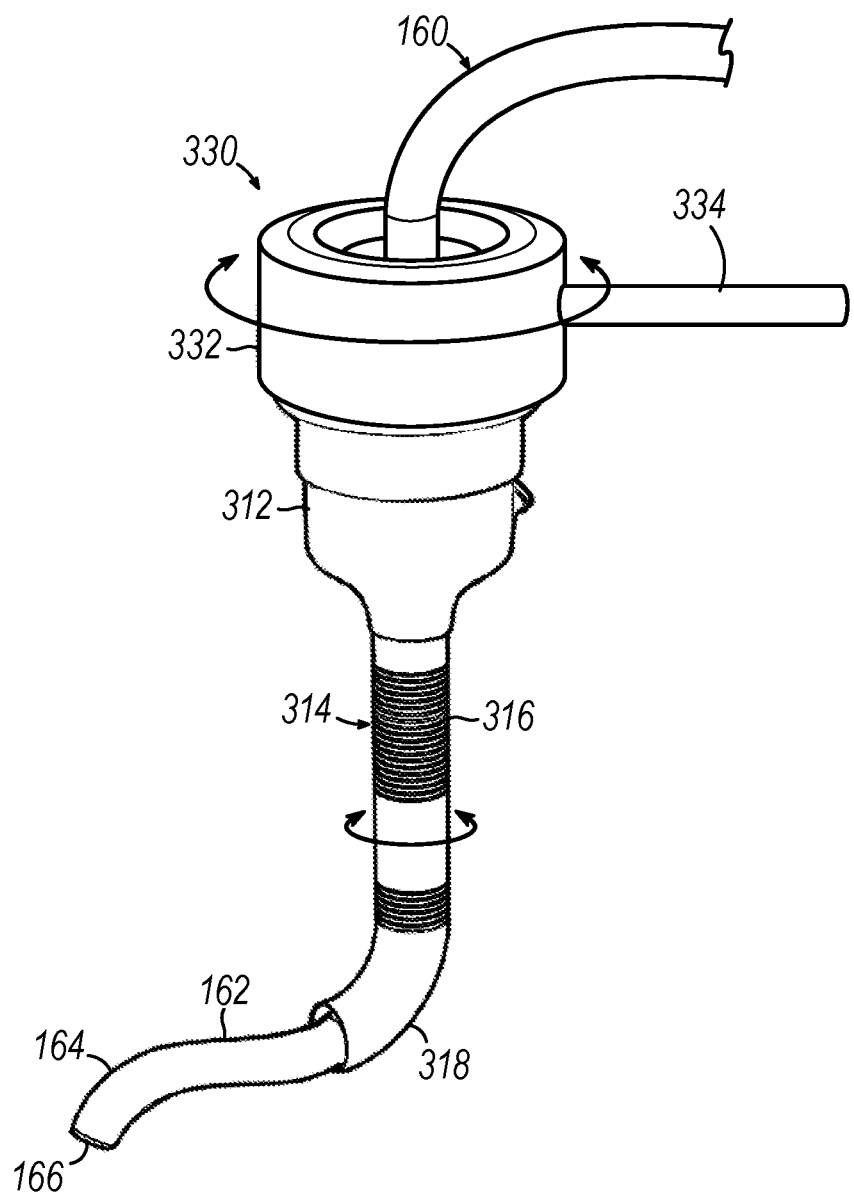
FIG. 25 depicts a perspective view of another example of a cannula having an angled distal tip and a tip actuator, shown in combination with a deflectable shaft portion of a surgical scope.

In some instances, it may be desirable to utilize a cannula having a cannula tube that is configured to direct a surgical scope shaft along an angled axis via a rigid cannula tip rather than via an articulating cannula tip like those of cannulas (170, 224, 248) described above. FIGS. 23-25 described below show some versions of such cannulas, in which rotation (or "roll") of the cannula tube is manually driven.

FIGS. 23-24 show an example of a cannula (310) that is similar to cannula (170) except as otherwise described. Cannula (310) includes a proximal structure in the form of a cup (312) having an open proximal end, and a distal structure in the form of an elongate rigid tube (314) that extends distally from a distal end of cup (312). In the present version, tube (314) includes a proximal tube portion (316) that extends coaxially with cup (312) along a central primary axis of cannula (310), and an angled distal tip (318) that extends along an arcuate path such that a distal-most end of angled distal tip (318) defines a secondary axis that is angled relative to (i.e., deviates from) and intersects the primary axis. Whereas angled distal tip (318) is curved along the arcuate path in the present version, in other versions angled distal tip (318) may be straight along the secondary axis. The interiors of cup (312) and tube (314) cooperate to define a working channel (not shown) that is similar to working channel (176) and is sized and configured to slidably receive and guide surgical scope shaft (160) longitudinally therethrough along the primary and secondary axes. In the present example, scope shaft (160) is shown without outer sheath (154) of surgical scope (150). However, it will be appreciated that scope shaft (160) may be slidably housed within a rigid outer sheath similar to outer sheath (154) or within a flexible outer sheath similar to flexible outer sheath (214). In either configuration, a proximal end of the outer sheath may terminate at or proximal to the proximal end of cannula (310).

A proximal end of cannula tube (314) is rotatably coupled with a tapered distal end of cup (312) such that tube (314) is selectively rotatable relative to cup (312) about the primary axis to selectively orient angled distal tip (318), and thus surgical scope shaft (160), within a body cavity (C) of a patient (P). In the present version, a cannula tube actuator in the form of a rotatable collar (320) is mounted to a proximal end of cup (312) and is operatively coupled with tube (314) by a feature (not shown) housed within cannula (310). Rotatable collar (320) is selectively rotatable by a user relative to cup (312) about the primary axis to rotate tube (314) relative to cup (312). Rotatable collar (320) includes a plurality of user gripping features in the form of ridges (322) to facilitate manual rotation of collar (320) by the user. Various other types of user gripping features may be provided in other versions. Rotatable collar (320) and tube (314) may be configured to rotate a full 360 degrees relative to cup (312), or any lesser range of rotation, for example as limited by one or more rotary stop features (not shown). As shown, rotatable collar (320) has an annular configuration with a central opening through which surgical scope (150) is directed. In use, a surgeon may rotate collar (320) to orient deflectable distal shaft portion (162) of scope shaft (160) generally toward a target zone within body cavity (C), thus providing gross positioning of scope distal tip section (166). Additionally, the surgeon may selectively control insertion, articulation, and roll of scope shaft (160), for example via drive mechanism (148) of robotic arm (140), to provide fine positioning of scope distal tip section (166) within body cavity (C).

FIG. 25 shows another example of a cannula (330) that is similar to cannula (310) described above except as otherwise described below. Cannula (330) includes cup (312) and rotatable tube (314) of cannula (310) and is shown in combination with surgical scope shaft (160). Unlike cannula (310), cannula (330) includes a cannula tube actuator in the form of a rotatable collar (332) having a rudder (334) that projects radially outwardly from collar (332). Collar (332) is rotatable relative to cup (312) about the primary axis to rotate tube (314) relative to cup (312), where rotation of collar (332) may be controlled by actuating rudder (334). In some versions, collar (332) may be omitted, and rudder (334) may be pivotably coupled with cup (312) and operatively coupled with tube (314) such that pivoting of rudder (334) relative to cup (312) operates to rotation tube (314) relative to cup (312). Additionally, cannulas (310, 330) may include or be used in combination with a locking feature operable to releasably lock rotatable collar (320, 332) and/or rudder (334) in a desired rotational orientation during a surgical procedure. In one such example, any one or more of these features may be releasably locked in place via grounding to a stationary structure, such as a table, a stationary arm, or a stationary surgical device, such as a liver retractor holder, for example.

Figure 26:
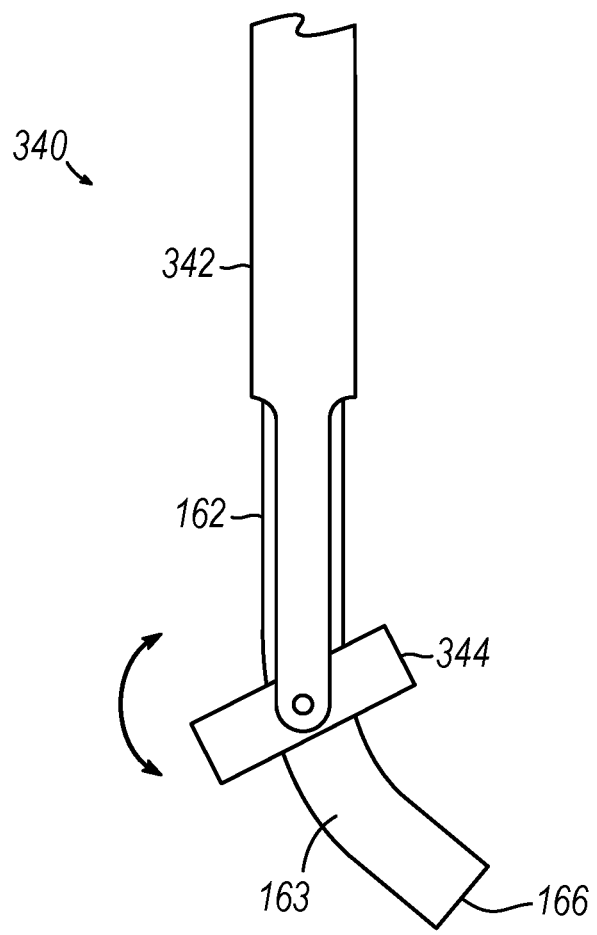
FIG. 26 depicts a side elevational view of a distal portion of another example of a cannula having an actuatable distal tip member, shown in combination with a deflectable shaft portion of a surgical scope.

FIG. 26 shows a distal portion of an example of an alternative cannula (340) that includes a cup (not shown) and a cannula tube (342) having a ring (344) pivotably coupled to its distal end about a pivot axis that extends transversely to a primary cannula axis defined by cannula tube (342). Ring (344) may be operatively coupled with any suitable actuator, such as either of collars (320, 332) or rudder (334) described above. Accordingly, manipulation of the actuator by a user may drive ring (344) to pivot relative to cannula tube (342) to a desired orientation to thereby angularly orient deflectable distal shaft portion (162) of surgical scope shaft (160) along a secondary axis that is angled relative to the primary axis of cannula (340).

It will be appreciated that any of the examples of cannulas described herein may be configured such that its cannula tube is rotatably coupled with its respective proximal structure (e.g., a cup or hub) such that rotation (or "roll") of the cannula tube relative to the proximal structure may be manually driven by a user-engageable actuator, such as any of actuators (320, 332, 334) described above, or may be powered via a motorized drive mechanism such as drive mechanism (148) of robotic arm (140) or remote drive mechanism (282).

VIII. Example of a Surgical Scope System with Cannula Roll Control

As described above, articulation of cannulas (170, 224, 248, 278) may be powered by motorized drive mechanism (148) of robotic arm (140) or by a remotely located motorized drive mechanism (282). Additionally, roll of cannula tube (314) relative to cup (312) may be manually driven by a user-engageable actuator (320, 332, 334). In some instances, it may be desirable to provide a version of robotic system (130) in which roll of the cannula tube relative to its proximal structure (e.g., cup or hub) is powered by a motorized drive mechanism controlled by master controller (132). As described below, such a configuration of robotic system (130) may be capable of controlling the surgical scope as well as cannula roll to orient the surgical scope to provide suitable visualization intracorporeally within the body cavity while also minimizing risk of collision between the extracorporeal portions of the surgical scope and other surgical instruments controlled by robotic system (130).

Figure 27:
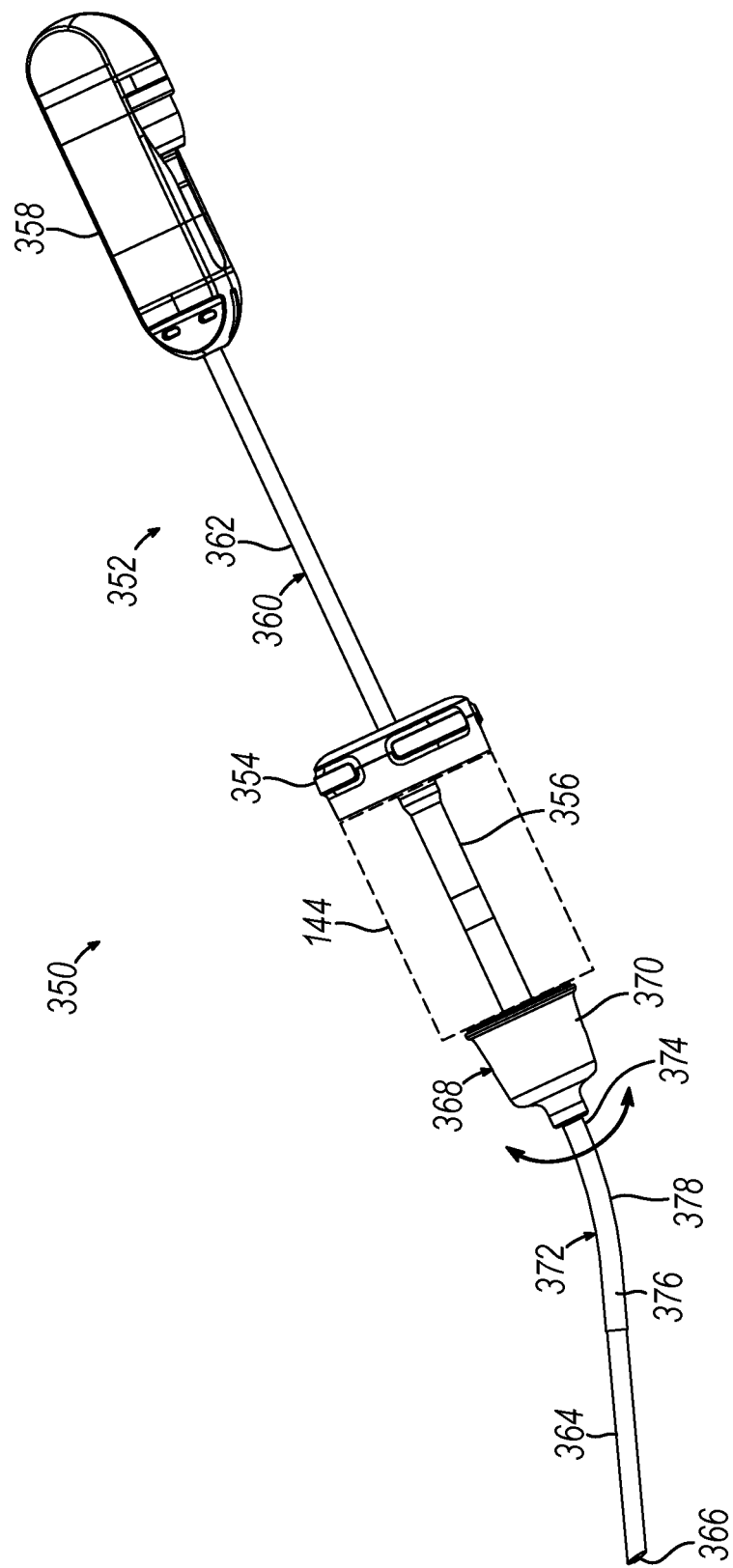
FIG. 27 depicts a side elevational view of an example of a robotic arm system that includes a surgical scope and a cannula mounted to a robotic arm head, shown schematically.
Figure 28:
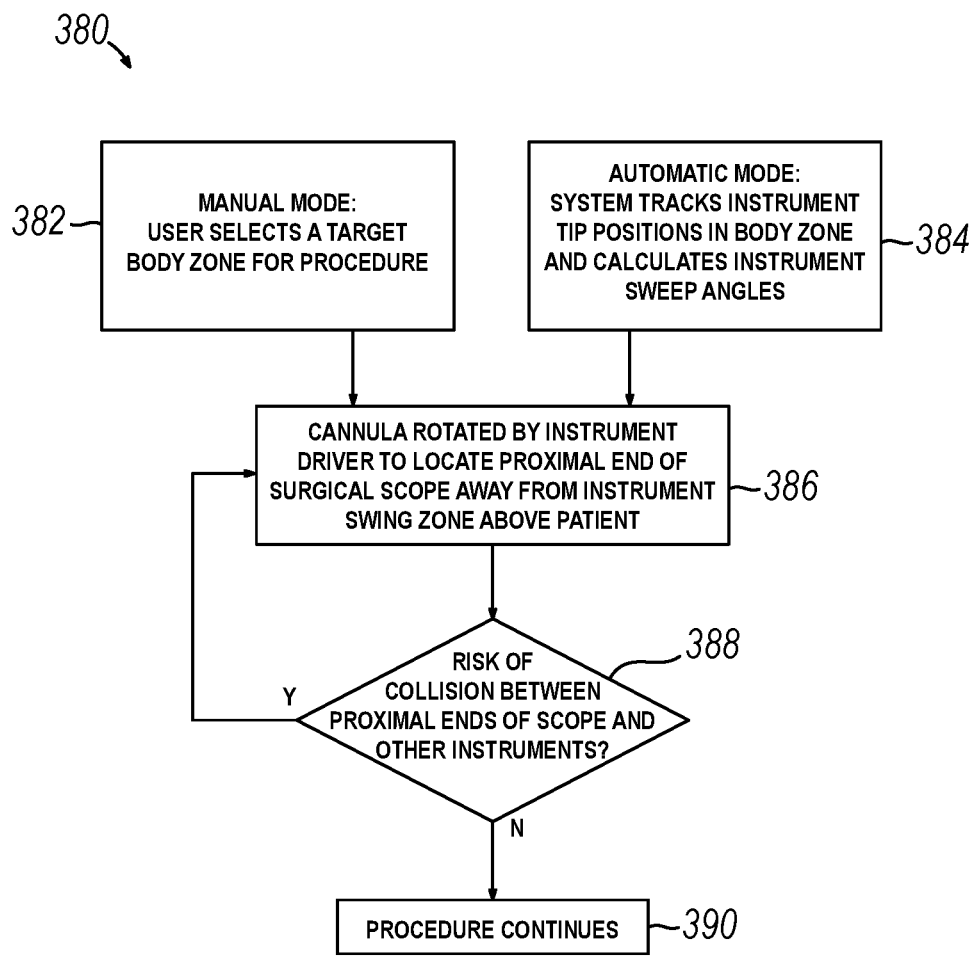
FIG. 28 depicts an example of a method for operating the robotic arm system of FIG. 27.

FIGS. 27-28 show an example of a robotic arm system (350) that includes robotic arm head (144) of robotic system (130) described above. A surgical scope (352) is removably coupled to robotic arm head (144) such that surgical scope (352) is positionable and actuatable by robotic arm (140). Surgical scope (352) includes a scope base (354) that is similar to scope base (152) and has a nosecone (356), a scope camera unit (358) arranged proximal to scope base (354), and a scope shaft (360) that extends distally from scope camera unit (358) and through scope base (354).

Scope shaft (360) may be similar to scope shaft (160) and includes a rigid proximal shaft portion (362) that extends distally from a proximal end of scope camera unit (358), and a deflectable distal shaft portion (364) that extends distally from a distal end of rigid proximal shaft portion (362). Deflectable distal shaft portion (364) includes a distal tip section (366) having an optical module with a lens operable to provide visualization of a target surgical site within a body cavity. Deflectable distal shaft portion (364) may also include an articulation section similar to articulation section (164).

Robotic arm system (350) further includes a cannula (368) having a cup (370) that defines a central primary axis of cannula (368) and may include an inner seal member similar to seal member (180). An angled tube (372) extends distally from, and is rotatably coupled with, a tapered distal end of cup (370). Angled tube (372) includes a proximal tube portion (374) that extends at a first angle to the primary axis or alternatively may be coaxial with the primary axis; and a distal tube portion (376) that extends along a secondary axis at a second angle to the primary axis, such as approximately 20 degrees. A bend section (378) is positioned between proximal and distal tube portions (374, 376) and defines a remote center of motion ("RCM") of cannula (368). With bend section (378) defining a RCM, robotic system (10, 28) may be configured to maintain bend section (378) in a substantially stationary position relative to the patient's body wall (W) during rotation of angled tube (372) relative to the body wall (W), as described below.

Angled cannula tube (372) is operatively coupled with nosecone (356) of scope base (354), for example via a direct connection, such that "roll" rotation of nosecone (356) by drive mechanism (148) of robotic arm head (144) drives "roll" rotation of tube (372) relative to cup (370) and relative to the patient's body wall (W). Accordingly, drive mechanism (148) is operable to drive roll of cannula tube (372) relative to cannula cup (370); as well as longitudinal actuation, articulation, and roll of scope shaft (360) relative to cannula (368). In some versions, a proximal end of cup (370) may be docked to a distal end of robotic arm head (144), for example with a structure similar to cannula docking plate (158), to thereby mechanically ground cup (370) relative to head (144).

FIG. 28 shows an example of a method (380) of operating robotic arm system (350) in the context of a surgical procedure. In this surgical procedure, cannula tube (372) at its bend section (378) is positioned within a body wall (W) of a patient such that distal tube portion (376) is positioned intracorporeally within the body cavity (C) while proximal tube portion (374) and cup (370) are positioned extracorporeally above the body wall (W). Additionally, one or more other surgical instruments extend through the body wall (W) at one or more other locations and are controlled by respective robotic arms (140) of robotic system (130).

As shown in FIG. 28, robotic arm system (350) may be operated in a manual mode or in an automatic mode. In manual mode, method (380) initiates with step (382) in which the user identifies for robotic system (130), via input to master controller (132), a target body zone within the body cavity in which the surgical procedure will be performed. Alternatively, in automatic mode, method (380) initiates with step (384) in which robotic system (130), via master controller (132), identifying the target body zone and tracking the positions within the body cavity (C) in that body zone of the distal tips (i.e., end effectors) of other surgical instruments controlled by other robotic arms (140) of robotic system (130). Based on the determined positions and movement patterns of the distal tips of the other surgical instruments, master controller (132) calculates an operating sweep angle for each surgical instrument. Based on the surgical instrument operating sweep angles determined in automatic mode, or the target body zone input by the user in manual mode, master controller (132) may determine an instrument swing zone in which the proximal ends of the other surgical instruments and their respective robotic arm heads (144) operate in the workspace above the patient during the surgical procedure.

Whether in manual mode or automatic mode, method (380) then proceeds to step (386). At this stage, master controller (132) controls robotic arm system (350) to activate drive mechanism (148) to rotate cannula tube (372) to position scope camera unit (358) and rigid proximal shaft portion (362) of surgical scope (352) (i.e., the extracorporeal portions of surgical scope (352)) away from the determined instrument swing zone, and to orient surgical scope distal tip section (366) toward the target body zone and the surgical site. Due to the angled shape of angled cannula tube (372), rotation of cannula tube (372) relative to the patient body wall effectively swings the extracorporeal proximal portion of surgical scope (352) away from the instrument swing zone, thereby increasing a distance between scope camera unit (358) and the extracorporeal proximal ends of the other surgical instruments. This may tend to minimize risk of collision between the proximal ends of the surgical instruments and scope camera unit (358); as well as collision between the various robotic arm heads (144) controlling surgical scope (352) and the other surgical instruments.

At step (388), master controller (132) assesses whether there is a risk of the extracorporeal proximal portion of surgical scope (352) entering the determined instrument swing zone such that there would be an ongoing risk of collision between surgical scope (352) and the surgical instruments or between their respective robotic arm heads (144). If master controller (132) determines that such a risk is present, then it repeats steps (386, 388) as many times as necessary until determining that no such risk is present, or that such a risk is present at less than or equal to a predetermined acceptable level. Upon determining no risk, or a predetermined acceptable level of risk, master controller (132) then proceeds with controlling robotic arms (140) to perform the surgical procedure, as indicated by step (392).

IX. Example of a Modular Surgical Scope System

During a surgical procedure, the distal lens of a surgical scope may accumulate bodily fluids and/or debris that may obstruct or otherwise reduce visualization such that the lens requires cleaning before the procedure can proceed effectively. Accordingly, it may be desirable to provide a surgical scope that is constructed to enable efficient disassembly for such cleaning, and efficient reassembly and positioning subsequent to such cleaning.

A. Overview of Modular Surgical Scope System

Figure 29:
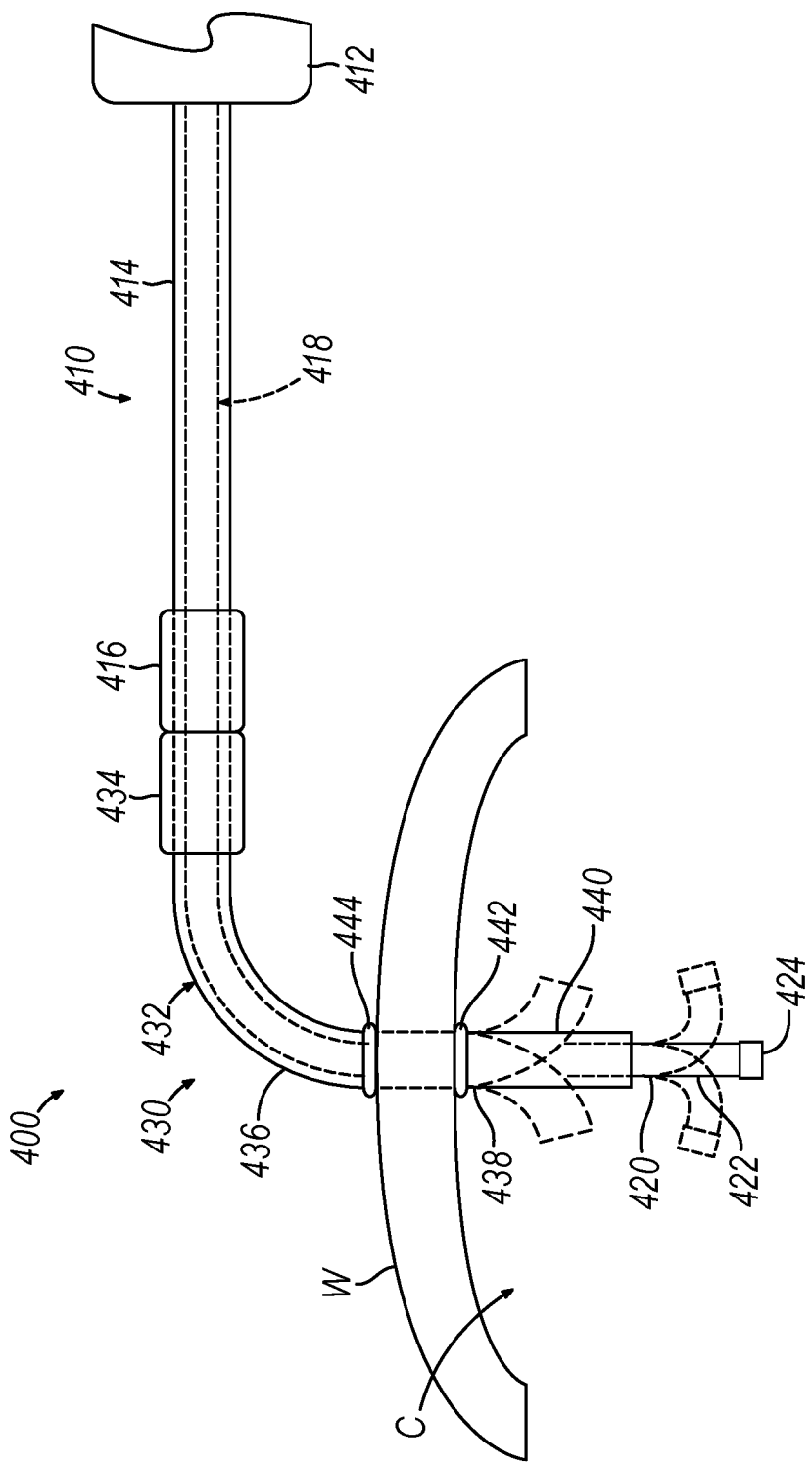
FIG. 29 depicts a schematic side view of an example of a modular surgical scope system, showing a surgical scope and a cannula of the system in a connected state.

FIG. 29 shows an example of a surgical scope system (400) having a modular construction that enables efficient disassembly and sequent reassembly for cleaning during a surgical procedure. Specifically, as described in greater detail below, surgical scope system (400) may be quickly and easily disassembled to gain access to scope distal tip section (424) without removing the corresponding cannula structure from the patient, and without retracting scope shaft (418) proximally through the full length of its outer sheath (414).

Surgical scope system (400) includes a proximal delivery structure in the form of a surgical scope (410) and a distal guide structure in the form of a cannula (430), where a distal end of surgical scope (410) is configured to releasably couple with a proximal end of cannula (430). Surgical scope (410) includes a scope base (412) (shown schematically) configured to releasably couple to a motorized drive mechanism of a robotic arm head, such as drive mechanism (148) of robotic arm head (144). An elongate scope sheath (414) extends distally from scope base (412) and terminates at a first connection member (416). Surgical scope (410) further includes a scope shaft (418) that extends distally from and is actuatable by scope base (412) and is slidably disposed within scope sheath (414) and is configured to extend and retract though cannula (430). Scope shaft (418) includes a deflectable distal shaft portion (420) having a scope articulation section (422) and a scope distal tip section (424) that includes an optical module having a lens that provides visualization within body cavity (C). In some versions, scope shaft (418) may further include a rigid proximal shaft portion that extends proximally from deflectable distal shaft portion (420) to scope base (412).

Cannula (430) includes an elongate cannula sheath (432) that terminates proximally at a second connection member (434) configured to releasably couple with first connection member (416) of surgical scope (410), for example in the manner described below in connection with FIGS. 32A-32B. Cannula sheath (432) includes a proximal sheath portion (436) configured to be positioned extracorporeally, and a distal sheath portion (438) configured to be inserted through a body wall (W) such that the distal end of distal sheath portion (438) is positioned intracorporeally within body cavity (C). The distal end of distal sheath portion (438) includes an articulation section (440) configured to articulate within body cavity (C) in one or more planes. Such articulation of distal sheath portion (438) may be driven by drive mechanism (148), for example via one or more articulation drivers (480) (see FIGS. 32A-32B) that extend longitudinally from scope base (412) to distal sheath portion (438), through connection members (416, 434). Accordingly, drive mechanism (148) may be configured drive articulation of both scope shaft (418) and cannula (430) to suitably orient distal tip section (424) of scope shaft (418) within body cavity (C).

At least proximal sheath portion (436) of cannula sheath (432) may be formed with a deflectable (e.g., flexible) construction that enables the extracorporeal portion of surgical scope system (400) to be draped away from the insertion site in body wall (W), as seen in FIG. 29. In some versions, an entirety of each of cannula sheath (432) and scope sheath (414) may be deflectable (e.g., flexible) to facilitate remote positioning of robotic arm head (144) and scope base (412).

Distal sheath portion (438) further includes a retention feature in the form of an annular flange (442) located proximal the articulation section of distal sheath portion (438). Flange (442) is configured to abut an interior surface of body wall (W) such that a user may reliably position the distal end of distal sheath portion (438) at a predetermined depth within body cavity (C), based on tactile feedback during insertion. Optionally, cannula sheath (432) may further include a second retention feature in the form of a proximal annular flange (444) spaced proximally from distal annular flange (442). Proximal flange (444) may be configured to abut an exterior surface of body wall (W) when cannula sheath (432) is inserted, and thereby cooperate with distal flange (442) to more securely stabilize cannula (430) relative to body wall (W), with the distal end of cannula (430) being positioned at a predetermined depth within body cavity (C). Flanges (442, 444) may be formed integrally with or otherwise affixed to cannula sheath (432) such that flanges (442, 444) are non-adjustable. Alternatively, flanges (442, 444) may be selectively positionable along a length of cannula sheath (432).

FIGS. 30A-30D show an example of a deployment of surgical scope system (400) with respect to a patient body wall (W) and body cavity (C). In the present version, surgical scope (410) is shown with a first user gripping feature (426) arranged proximal to first connection member (416), and cannula (430) is shown with a second user gripping feature (446) arranged distal to second connection member (434). A user may grasp gripping features (426, 446) to facilitate insertion and removal of cannula (430), and attachment and detachment of surgical scope (410) relative to cannula (430). It will be appreciated that gripping features are merely optional and may be omitted in other versions, such as is shown in FIG. 29.

Figure 30A:
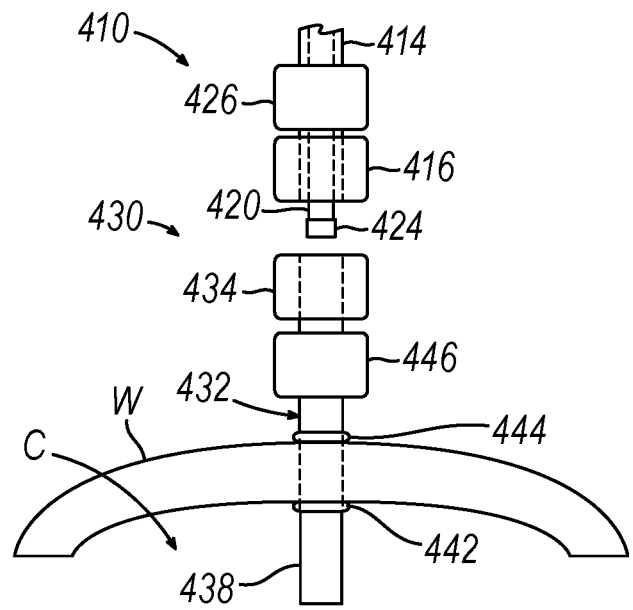
FIG. 30A depicts a schematic side view of the modular surgical scope system of FIG. 29, showing the surgical scope separated from but aligned with the cannula.
Figure 30B:
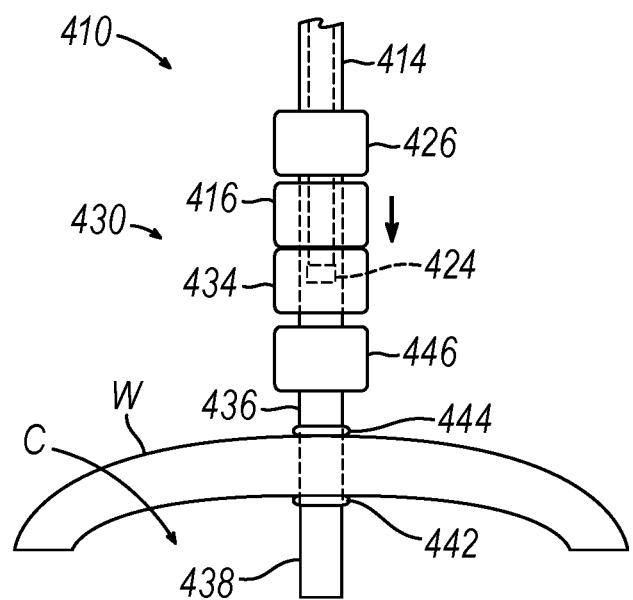
FIG. 30B depicts a schematic side view of the modular surgical scope system of FIG. 29, showing a connection member of the surgical scope mated with a connection member of the cannula.
Figure 30C:
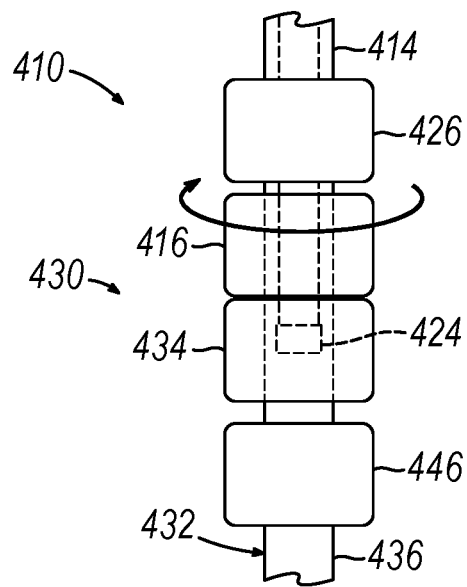
FIG. 30C depicts a schematic side view of the modular surgical scope system of FIG. 29, showing the connection members having been rotated relative to one another into an engaged state in which an articulation driver of the cannula is engaged with an articulation driver of the surgical scope.

As shown in FIG. 30A, cannula sheath (432) has been inserted distally through body wall (W), for example with use of a removable obturator (not shown), such that annular flanges (442, 444) respectively abut the interior and exterior surfaces of body wall (W). Accordingly, the distal end of cannula sheath (432) is maintained at a predetermined depth within body cavity (C). As shown in FIGS. 30A-30B, first connection member (416) of surgical scope (410) is aligned coaxially with second connection member (434) of cannula (430). Distal tip section (424) of scope shaft (418) may be partially advanced from scope sheath (414) to assist with proper alignment as shown; or distal tip section (424) may be fully retracted within scope sheath (414). As shown in FIGS. 30B-30C, connection members (416, 434) are brought into contact with one another and manipulated to lockingly engage one another. In the present version, connection members (416, 434) are configured to interlock with a twisting motion in which connection members (416, 434) are rotated relative to one another through a predetermined angular range. In that regard, the mating portions of connection members (416, 434) may include threads, bayonet lugs, or any other suitable interlocking features that will be readily apparent to those skilled in the art in view of the teachings herein.

Figure 30D:
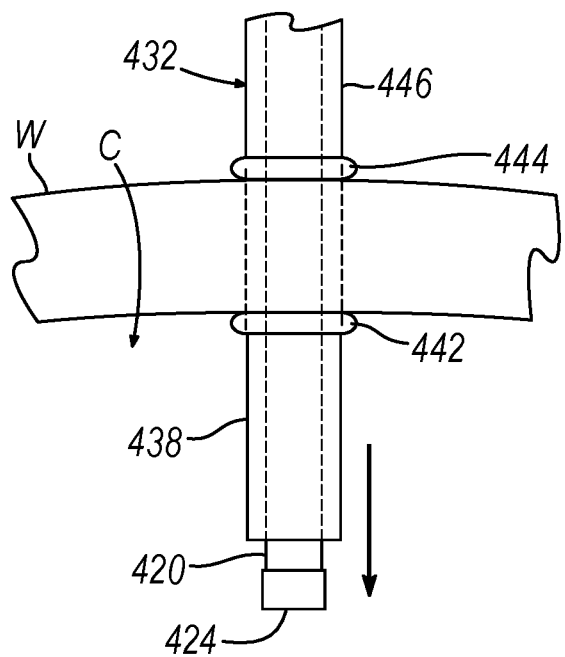
FIG. 30D depicts an enlarged schematic side view of the modular surgical scope system of FIG. 29, showing distal insertion of a deflectable distal shaft portion of the surgical scope through the cannula and into the body cavity of a patient.

As shown in FIG. 30D, with connection members (416, 434) interlocked, scope shaft (418) may be advanced distally through connection members (416, 434), cannula sheath (432), and into body cavity (C). As shown in FIG. 29, distal sheath portion (438) of cannula (430) and/or deflectable distal shaft portion (420) of surgical scope (410) may be articulated to suitably orient distal tip section (424) of surgical scope shaft (418) within body cavity (C).

The modular construction of surgical scope system (400) enables surgical scope system (400) to be quickly and easily disassembled during a surgical process to gain access to the lens of distal tip section (424) for an intraoperative cleaning or other service, for example. To accomplish this, the steps illustrated in FIGS. 30A-30D need simply be performed in reverse order. Specifically, scope shaft (418) is retracted proximally through cannula (430) toward scope sheath (414). Connection members (416, 434) are then manipulated to disengage one another and permit separation of surgical scope (410) from cannula (430). Upon separating surgical scope (410) from cannula (430), distal tip section (424) can be accessed at the distal end of surgical scope (410) for cleaning or other servicing. Once complete, surgical scope (410) and cannula (430) may be quickly and easily reassembled in the same manner described above. Advantageously, this approach avoids having to remove cannula (430) from body wall (W) or having to retract scope shaft (418) fully proximally through a proximal end of scope sheath (414) in order to gain access for cleaning or servicing.

Though not shown, surgical scope (410) and/or cannula (430) may include one or more inner seal members, which may be similar to inner seal member (180), configured to maintain insufflation of body cavity (C) both in attached and detached states of surgical scope (410) relative to cannula (430). Accordingly, surgical scope (410) may be separated from cannula (430) during a surgical procedure to access scope distal tip section (424), without disrupting the position of cannula (430) and without compromising insufflation of body cavity (C).

B. Example of an Integrated Scope Tip Cleaning Feature

Figure 31:
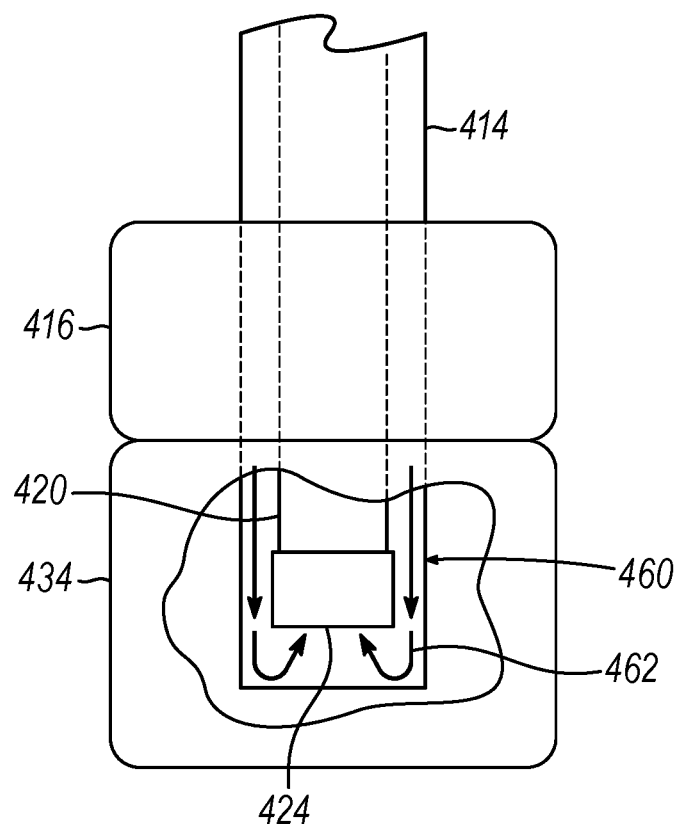
FIG. 31 depicts an example of a method of cleaning a distal tip section of the surgical scope of the modular surgical scope system of FIG. 29 within the connection member of the cannula.

FIG. 31 shows an example of a variation of surgical scope system (400) in which second connection member (434) of cannula (430) includes an inner cleaning chamber (460), which may be sealed at proximal and distal ends by respective seal members (not shown). In use, distal tip section (424) may be retracted proximally into cleaning chamber (460), and then cleaning fluid (462) may be flushed through cleaning chamber (460) to clean distal tip section (424), where the inner seal members included within second connection member (434) inhibit fluid egress into cannula sheath (432). Flow of the cleaning fluid (462) may be directed by an external pump (not shown) that is actuated or activated by drive mechanism (148) or an alternative mechanism. In this manner, distal tip section (424) of scope shaft (418) may be effectively cleaned intraoperatively without disconnecting surgical scope (410) from cannula (430) or disrupting the position of cannula (430).

C. Example of a Connection Mechanism for Surgical Scope System

Figure 32A:
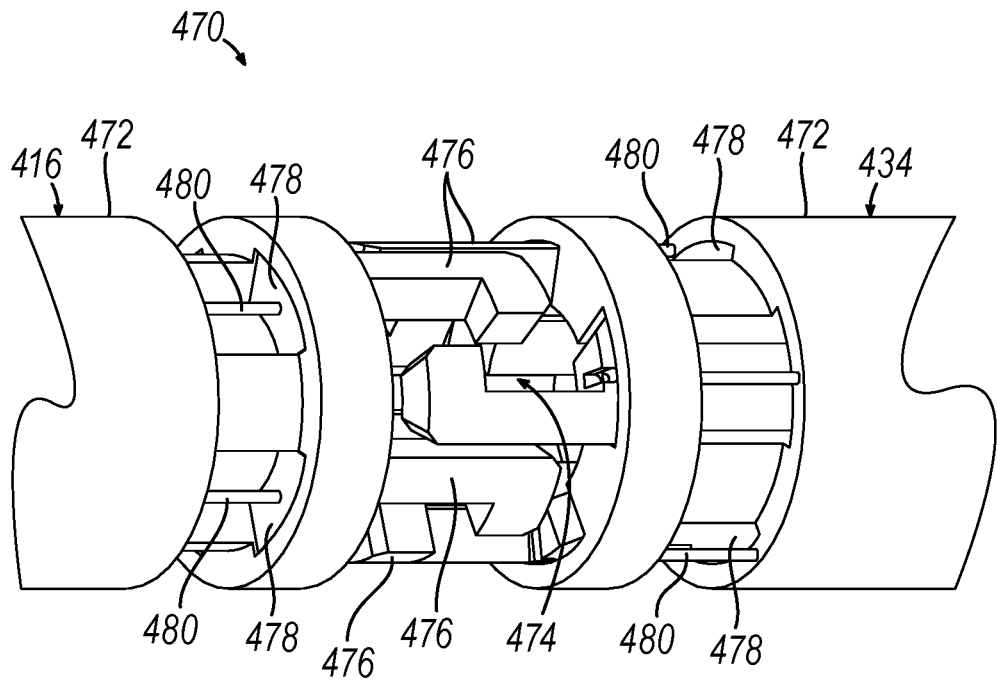
FIG. 32A depicts a perspective view of an example of a connection mechanism defined by the connection members of the modular surgical scope system of FIG. 29, showing cannula articulation drivers of the connection mechanism in an unengaged state.
Figure 32B:
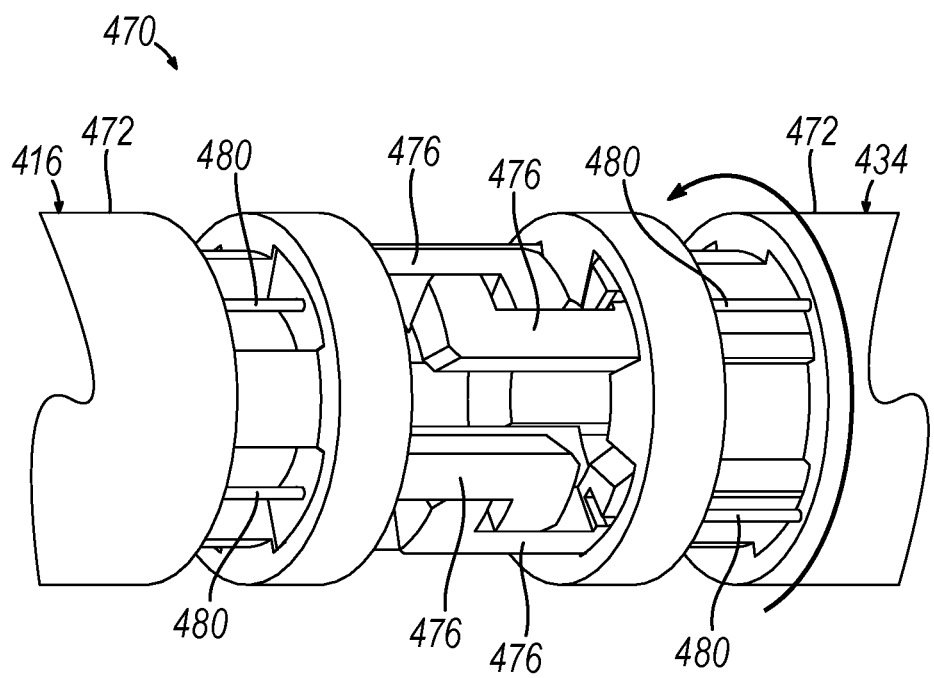
FIG. 32B depicts a perspective view of the connection mechanism of FIG. 32A, showing the cannula articulation drivers in an engaged state.

FIGS. 32A-32B show an example of a connection mechanism (470) defined by first and second connection members (416, 434) of surgical scope system (400) described above. For illustration purposes, an outer wall of first and second connection members (416, 434) is omitted from view. First connection member (416) includes a first annular frame (472) having a first central lumen (474) configured to slidably receive scope shaft (418), and a first plurality hook-shaped interlocking members (476) arranged circumferentially about first central lumen (474). Each first interlocking member (476) is slidable longitudinally within a respective channel (478) formed in first annular frame (472). First annular frame (472) may include one or more stop features configured to limit such longitudinal movement of first interlocking members (476). A proximal end of each first interlocking member (476) is coupled with a respective articulation driver shown in the form of a tendon (480). Each tendon (480) extends proximally through scope sheath (414) to scope base (412) and is actuatable by a drive mechanism, such as motorized drive mechanism (148) of robotic arm head (144).

Second connection member (434) is configured similar to first connection member (416) and includes a second annular frame (472) having a second central lumen (474) configurated to slidably receive scope shaft (418); and a second plurality hook-shaped interlocking members (476) arranged circumferentially about second central lumen (474). Each second interlocking member (476) is slidable longitudinally within a respective channel (478) formed in second annular frame (472), and second annular frame (472) may include one or more stop features configured to limit such longitudinal movement of second interlocking members (476). A distal end of each interlocking member (476) is coupled with a respective articulation driver shown in the form of a tendon (480). Each tendon (480) extends distally through cannula sheath (432) and is anchored to distal sheath portion (438) at cannula articulation section (440).

As described above, after being aligned coaxially, first and second connection members (416, 434) are configured to lockingly engage one another in response to relative rotation between first and second connection members (416, 434). As shown in FIGS. 32A-32B, such rotation results in each first interlocking member (476) interlocking with a respective second interlocking member (476). Though not shown, connection members (416, 434) may include one or more additional interlocking features such as threads, lugs, etc. configured to interlock first annular frame (472) with second annular frame (472) in response to such relative rotation. In the engaged state shown in FIG. 32B, each first tendon (480) is coupled with a respective second tendon (480) via a respective pair of interlocking members (476). Accordingly, longitudinal actuation of the first tendon (480) by drive mechanism (148) longitudinally actuates the respective second tendon (480) to thereby articulate cannula (430) at cannula articulation section (440) in a respective direction.

In the present example, the sets of tendons (480) and interlocking members (476) are arranged circumferentially at 90 degree intervals such that a first diametrically opposed pair of tendons (480) and interlocking members (476) cooperate in a pull-pull manner to articulate distal sheath portion (438) of cannula (430) in opposing first and second directions in a first articulation plane. Additionally, a second diametrically opposed pair of tendons (480) and interlocking members (476) cooperate in a pull-pull manner to articulate distal sheath portion (438) of cannula (430) in opposing first and second directions in a second articulation plane that perpendicularly intersects the first articulation plane. In other versions, cannula (430) of surgical scope system (400) may be configured to articulate in various other quantities of articulation planes. Additionally, in other versions of connection mechanism (470), connection members (416, 434) and interlocking members (476) may be configured to releasably connect in various other suitable manners that will be readily apparent to those skilled in the art in view of the teachings herein.

D. Example of an Alternative Connection Member

Figure 33:
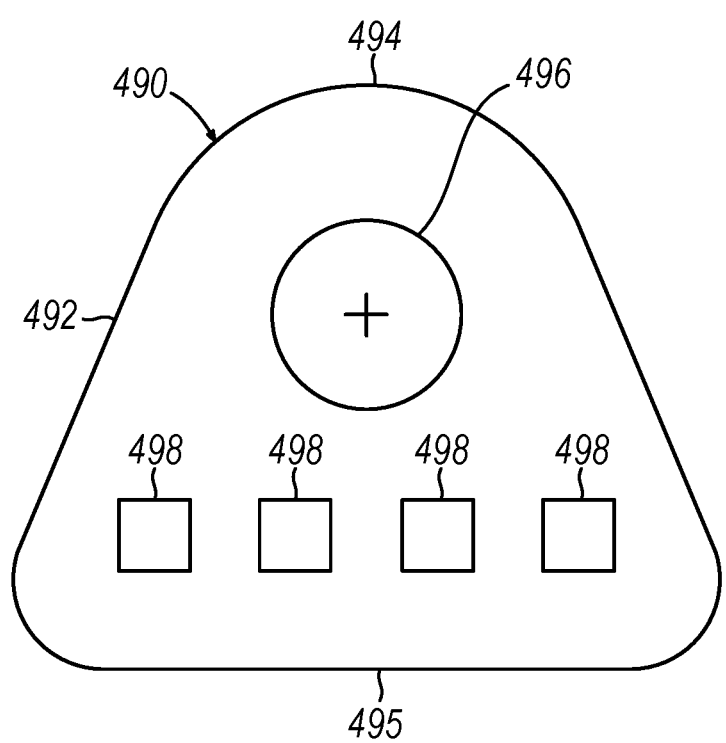
FIG. 33 depicts a schematic cross-sectional view of another example of a connection mechanism configured for use with the modular surgical scope system of FIG. 29.

FIG. 33 shows a cross-sectional view of another example of a connection member (490) configured for use with modular surgical scope system (400). Similar to connection members (416, 434), a first connection member (490) may be provided at the distal end of scope sheath (414); and a second connection member (490) may be provided at the proximal end of cannula sheath (432). Connection member (490) includes a frame (492) having a rounded trapezoidal shape having a tapered side (494) and a flared side (495). A scope shaft lumen (496) extends longitudinally through frame (492) along tapered side (494), coaxially with scope sheath (414) and cannula sheath (432). Scope shaft lumen (496) is configured to slidably receive scope shaft (418). A linear array of articulation driver lumens (498) extend longitudinally through frame (492) along flared side (495), where each lumen (498) is configured to slidably receive a respective articulation driver (e.g., tendon, cable, etc.), which may be similar to tendons (480). Though not shown, connection member (490) further includes a plurality of interlocking members that may be similar to interlocking members (476) and are configured to releasably interlock with an opposing set of interlocking members of the opposing connection member (490), for example in response to relative rotation or translation of connection members (490).

The linear arrangement of articulation driver lumens (498) and the corresponding articulation drivers provides a configuration that enables single plane articulation of cannula sheath (432) while providing a constant path length change across all the articulation drivers during articulation. Such a configuration may be combined with providing all or a portion of cannula sheath (432) with the ability to rotate relative to connection member (490).

X. Example of a Swivel Support Structure for Flexible Surgical Cannula

As described above in connection with FIGS. 29-30D, it may be desirable to employ a cannula having a flexible cannula sheath (also referred to as a cannula tube) to enable a proximal extracorporeal portion of the cannula to be draped away from cannula insertion site and thereby minimize a footprint of the cannula and the surgical scope in the workspace above the patient. In some instances, it may be desirable to provide an additional structure capable of supporting the flexible extracorporeal portion of the cannula in each of a straight configuration and a bent configuration to accommodate various stages of a surgical procedure.

Figure 34:
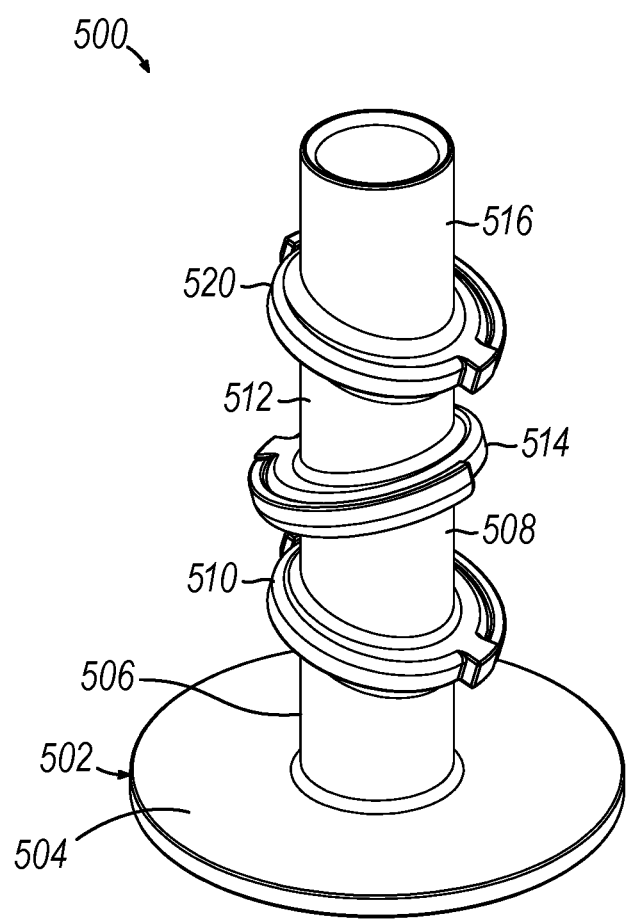
FIG. 34 depicts a perspective view of an example of a swivel support structure configured for use with a surgical cannula.
Figure 35A:
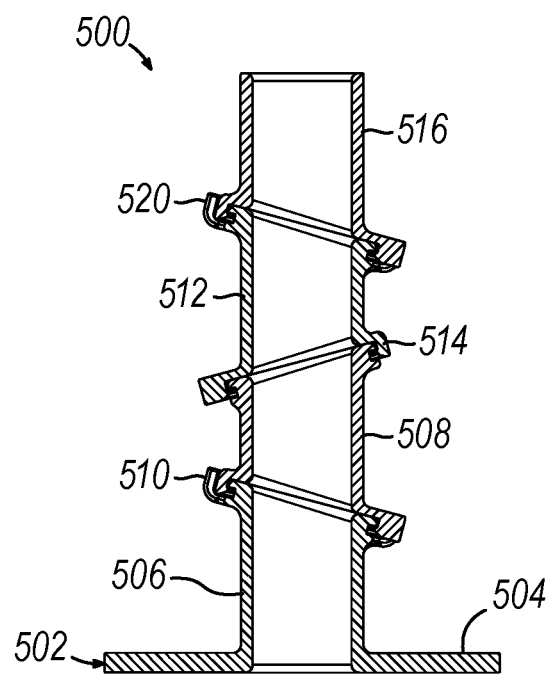
FIG. 35A depicts a side cross-sectional view of the swivel support structure of FIG. 29, shown in a straight state.

FIG. 34 shows an example of a swivel support structure (500) configured to support a flexible sheath (also referred to as a tube) of a cannula, such as cannula sheath (432) of cannula (430). Swivel support structure (500) includes a base (502) having an annular flange (504) and a first tubular link (506) integrally connected with and extending upwardly from cannular flange (504). A second tubular link (508) is pivotably coupled with a proximal end of first tubular link (506) at a first angled swivel joint (510); a third tubular link (512) is pivotably coupled with a proximal end of second tubular link (508) at a second angled swivel joint (514); and a fourth tubular link (516) is pivotably coupled with a proximal end of third tubular link (512) at a third angled swivel joint (520). Each angled swivel joint (510, 514, 520) defines a respective plane that is obliquely oriented relative to the central longitudinal axes of tubular links (506, 508, 516). Moreover, as best seen in FIG. 35A, these oblique planes of angled swivel joints (510, 514, 520) are angularly offset from each other in a staggered arrangement.

Figure 35B:
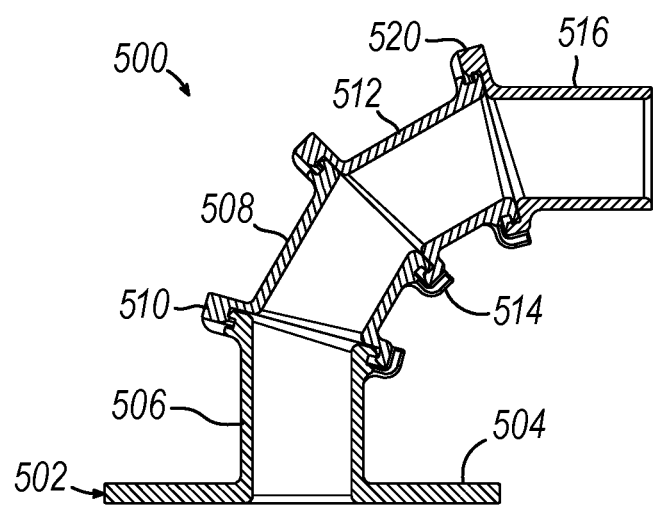
FIG. 35B depicts a side cross-sectional view of the swivel joint of FIG. 29, shown in an angled state.

In use, swivel support structure (500) may be provided in the straight configuration shown in FIGS. 34 and 35B to guide a cannula sheath distally into patient's body cavity. Specifically, annular flange (504) may be positioned against the exterior surface of the patient's body wall, and the flexible sheath of a cannula may be inserted distally through the open distal end of fourth tubular link (516). Subsequently, swivel support structure (500) may be transitioned to the angled state shown in FIG. 35B to support the cannula in a draped or bent state, for example as exhibited by cannula (430) in FIG. 29. Specifically, second tubular link (508) may be rotated 180 degrees relative to first tubular link (506) at first swivel joint (510); third tubular link (512) may be rotated 180 degrees relative to second tubular link (508) at second swivel joint (514); and fourth tubular link (516) may be rotated 180 degrees relative to first tubular link (506) at third swivel joint (518). Swivel support structure may be oriented in various intermediate angled states by rotating one or more of tubular links (506, 508, 512, 516) relative to one another by a desired degree at the respective one or more swivel joints (510, 514, 520).

XI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a proximal structure configured to be positioned extracorporeally relative to a patient; (b) a distal structure extending distally from the proximal structure and configured to be passed through a body wall and into a body cavity of the patient, wherein the distal structure cooperates with the primary structure to define a primary axis and a working channel sized and configured to receive and guide a surgical scope shaft distally therethrough along the primary axis, wherein the proximal structure has a greater maximum dimension in a direction transverse to the primary axis than the distal structure; and (c) an articulation feature at a distal end of the distal structure, wherein the articulation feature is configured to articulate relative to the proximal structure to direct the surgical scope shaft along a secondary axis that is angled relative to the primary axis.

Example 2

The apparatus of Example 1, wherein the distal structure comprises a rigid tube.

Example 3

The apparatus of any of the preceding Examples, wherein the proximal structure houses a seal member configured to form an air-tight seal against a surgical scope shaft directed along the working channel.

Example 4

The apparatus of any of the preceding Examples, wherein the proximal structure includes an access port that communicates with the working channel and is configured to direct insufflation gas into or from the body cavity.

Example 5

The apparatus of any of the preceding Examples, wherein the articulation feature is configured to articulate in a plane that includes or extends parallel to the primary axis.

Example 6

The apparatus of any of the preceding Examples, wherein the articulation feature comprises an articulation joint that includes a first joint link and a second joint link pivotably coupled together about a pivot axis that extends transversely to the primary axis, where the first and second joint links are rigid.

Example 7

The apparatus of any of the preceding Examples, further comprising at least one motor operatively coupled with the articulation feature, wherein the at least one motor is operable to drive articulation of the articulation feature.

Example 8

The apparatus of Example 7, wherein the at least one motor is operable to drive rotation of the distal structure relative to the proximal structure.

Example 9

The apparatus of any Examples 7 through 8, wherein the at least one motor is housed within the proximal structure.

Example 10

A system, comprising: (a) the apparatus of any of the preceding Examples; and (b) a surgical scope, including: (i) a scope base configured to be positioned extracorporeally relative to the patient, (ii) an outer sheath extending distally from the scope base and having a distal end coupled with the proximal structure, and (iii) a scope shaft that is longitudinally actuatable through the outer sheath and the cannula, wherein the scope shaft includes a proximal shaft portion and a deflectable distal shaft portion.

Example 11

The system of Example 10, wherein the deflectable distal shaft portion is flexible.

Example 12

The system of any of Examples 10 through 11, wherein the deflectable distal shaft portion includes a core and a resilient sheath that encircles the core, wherein the resilient sheath is resiliently biased toward a straight configuration.

Example 13

The system of any of Examples 10 through 12, further comprising a drive mechanism operatively coupled with the scope base and separated from the apparatus by a portion of the scope shaft, wherein the drive mechanism is operable to actuate the scope shaft relative to the apparatus.

Example 14

The system of Example 13, wherein the deflectable distal shaft portion includes an articulation section configured to articulate a distal end of the scope shaft relative to a remainder of the deflectable distal shaft portion, wherein the drive mechanism is operable to drive articulation of the articulation section.

Example 15

The system of any of Examples 13 through 14, further comprising a robotic arm that presents the drive mechanism.

Example 16

An apparatus comprising: (a) a proximal structure configured to be positioned extracorporeally relative to a patient, wherein the proximal structure is configured to receive a surgical scope shaft therethrough along an introductory axis; (b) a tube extending distally from the proximal structure and configured to be passed through a body wall and into a body cavity of the patient, wherein the tube cooperates with the proximal structure to define a working channel sized and configured to receive and guide the surgical scope shaft distally therethrough, wherein the working channel extends through the tube along a primary axis that is angled relative to the introductory axis; and (c) a motorized drive mechanism housed within the proximal structure, wherein the motorized drive mechanism is operable to actuate a first portion of the apparatus relative to a second portion of the apparatus such that a distal end of the apparatus is configured to direct the surgical scope shaft along a secondary axis that is angled relative to each of the primary axis and the introductory axis.

Example 17

The apparatus of Example 16, further comprising an articulation feature at a distal end of the tube, wherein the articulation feature is configured to articulate relative to the proximal structure to direct the surgical scope shaft along the secondary axis, wherein the motorized drive mechanism is operable to drive articulation of the articulation feature.

Example 18

The apparatus of any of Examples 16 through 17, wherein the tube is rotatable relative to the proximal structure about the primary axis, wherein the motorized drive mechanism is operable to drive rotation of the tube relative to the proximal structure.

Example 19

A system, comprising: (a) a support structure; (b) a motorized drive mechanism operatively coupled with the support structure; (c) a surgical scope, including: (i) a scope base coupled with the motorized drive mechanism, (ii) an outer sheath extending distally from the scope base, and (iii) a scope shaft that is actuatable through the scope base and the outer sheath by the motorized drive mechanism, wherein the scope shaft includes a proximal shaft portion and a deflectable distal shaft portion; and (d) a cannula, including: (i) a proximal structure configured to be positioned extracorporeally relative to a patient, wherein the proximal structure is coupled with a distal end of the outer sheath, (ii) a distal structure extending distally from the proximal structure and configured to be passed through a body wall and into a body cavity of the patient, wherein the distal structure cooperates with the proximal structure to define a primary axis and a working channel sized and configured to receive and guide the deflectable distal shaft portion therethrough along the primary axis, and (iii) an articulation feature configured to articulate to direct the deflectable distal shaft portion along a secondary axis that is angled relative to the primary axis.

Example 20

The system of Example 19, wherein the motorized drive mechanism is operable to drive articulation of the articulation feature of the cannula.

XII. Miscellaneous

The teachings herein may be combined with any one or more of the teachings disclosed in U.S. patent application Ser. No. 17/941,062, entitled "Bent Introducer Cannula for Surgical Scope in Robotic System," filed on Sep. 9, 2022, published as U.S. Pub. No. 2024/0081942 on Mar. 14, 2024, the disclosure of which is incorporated by reference herein in its entirety; U.S. patent application Ser. No. 17/941,059 entitled "Flexible Articulating Introducer Cannula for Surgical Scope in Robotic System," filed on Sep. 9, 2022, published as U.S. Pub. No. 2024/0081922 on Mar. 14, 2024, the disclosure of which is incorporated by reference herein in its entirety; and/or U.S. patent application Ser. No. 17/941,057, entitled "Remotely Driven Camera in Robotic System," filed on Sep. 9, 2022, published as U.S. Pub. No. 2024/0081932 on Mar. 14, 2024, the disclosure of which is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Some versions of the examples described herein may be implemented using a processor, which may be part of a computer system and communicate with a number of peripheral devices via bus subsystem. Versions of the examples described herein that are implemented using a computer system may be implemented using a general-purpose computer that is programmed to perform the methods described herein. Alternatively, versions of the examples described herein that are implemented using a computer system may be implemented using a specific-purpose computer that is constructed with hardware arranged to perform the methods described herein. Versions of the examples described herein may also be implemented using a combination of at least one general-purpose computer and at least one specific-purpose computer.

In versions implemented using a computer system, each processor may include a central processing unit (CPU) of a computer system, a microprocessor, an application-specific integrated circuit (ASIC), other kinds of hardware components, and combinations thereof. A computer system may include more than one type of processor. The peripheral devices of a computer system may include a storage subsystem including, for example, memory devices and a file storage subsystem, user interface input devices, user interface output devices, and a network interface subsystem. The input and output devices may allow user interaction with the computer system. The network interface subsystem may provide an interface to outside networks, including an interface to corresponding interface devices in other computer systems. User interface input devices may include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system.

In versions implemented using a computer system, a storage subsystem may store programming and data constructs that provide the functionality of some or all of the modules and methods described herein. These software modules may be generally executed by the processor of the computer system alone or in combination with other processors. Memory used in the storage subsystem may include a number of memories including a main random-access memory (RAM) for storage of instructions and data during program execution and a read only memory (ROM) in which fixed instructions are stored. A file storage subsystem may provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem in the storage subsystem, or in other machines accessible by the processor.

In versions implemented using a computer system, the computer system itself may be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the example of the computer system described herein is intended only as a specific example for purposes of illustrating the technology disclosed. Many other configurations of a computer system are possible having more or fewer components than the computer system described herein.

As an article of manufacture, rather than a method, a non-transitory computer readable medium (CRM) may be loaded with program instructions executable by a processor. The program instructions when executed, implement one or more of the computer-implemented methods described above. Alternatively, the program instructions may be loaded on a non-transitory CRM and, when combined with appropriate hardware, become a component of one or more of the computer-implemented systems that practice the methods disclosed.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
   (a) an apparatus, comprising:
      (i) a proximal structure configured to be positioned extracorporeally relative to a patient;
      (ii) a distal structure extending distally from the proximal structure and configured to be passed through a body wall and into a body cavity of the patient, wherein a primary axis extends through the distal structure and the proximal structure, and a working channel extends through the distal structure and the proximal structure, wherein the proximal structure has a greater maximum dimension in a direction transverse to the primary axis than a maximum dimension in a direction transverse to the primary axis of the distal structure; and
      (iii) an articulation feature at a distal end of the distal structure;
   (b) a surgical scope, comprising:
      (i) a scope base configured to be positioned extracorporeally relative to the patient;
      (ii) an outer sheath extending distally from the scope base and having a distal end coupled with the proximal structure; and
      (iii) a scope shaft that is longitudinally actuatable through the outer sheath and the working channel, wherein the scope shaft includes a proximal shaft portion and a deflectable distal shaft portion, wherein the working channel is sized and configured to receive and guide the scope shaft distally therethrough along the primary axis, wherein the articulation feature is configured to articulate relative to the proximal structure to direct the scope shaft along a secondary axis that is angled relative to the primary axis;
   (c) a drive mechanism operatively coupled with the scope base and separated from the apparatus by a portion of the scope shaft, wherein the drive mechanism is operable to actuate the scope shaft relative to the apparatus; and
   (d) a robotic arm configured to present the drive mechanism.

2. The system of claim 1, wherein the distal structure comprises a rigid tube.

3. The system of claim 1, wherein the proximal structure houses a seal member configured to form an air-tight seal against the scope shaft directed along the working channel.

4. The system of claim 3, wherein the proximal structure includes an access port that communicates with the working channel and is configured to direct insufflation gas into or from the body cavity.

5. The system of claim 1, wherein the articulation feature is configured to articulate in a plane that extends along the primary axis or extends parallel to the primary axis.

6. The system of claim 1, wherein the articulation feature comprises an articulation joint that includes a first joint link and a second joint link pivotably coupled together about a pivot axis that extends transversely to the primary axis, where the first and second joint links are rigid.

7. The system of claim 1, further comprising at least one motor operatively coupled with the articulation feature, wherein the at least one motor is operable to drive articulation of the articulation feature.

8. The system of claim 7, wherein the at least one motor is operable to drive rotation of the distal structure relative to the proximal structure.

9. The apparatus system of claim 7, wherein the at least one motor is housed within the proximal structure.

10. The system of claim 1, wherein the deflectable distal shaft portion is flexible.

11. The system of claim 10, wherein the deflectable distal shaft portion includes a core and a resilient sheath that encircles the core, wherein the resilient sheath is resiliently biased toward a straight configuration.

* * * * *